United States Patent [19]

Christensen et al.

[11] 4,226,870
[45] Oct. 7, 1980

[54] O-, N- AND CARBOXYL DERIVATIVES OF THIENAMYCIN

[75] Inventors: Burton G. Christensen, Metuchen; John Hannah, Matawan; William J. Leanza, Berkeley Heights; Ronald W. Ratcliffe, Matawan; David H. Shih, Edison, all of N.J.

[73] Assignee: Merck & Co., Inc., Rahway, N.J.

[21] Appl. No.: 861,246

[22] Filed: Dec. 16, 1977

Related U.S. Application Data

[63] Continuation-in-part of Ser. No. 733,652, Oct. 18, 1976, abandoned, which is a continuation-in-part of Ser. No. 634,294, Nov. 21, 1975, abandoned.

[51] Int. Cl.$^3$ .................. C07D 487/04; A61K 31/44; A61K 31/40
[52] U.S. Cl. ........................... 424/263; 260/245.2 T; 424/269; 424/270; 424/272; 424/273 R; 424/274; 546/272
[58] Field of Search ............... 260/326.31, 245.2 T; 424/274, 263, 272, 273; 546/272

[56] References Cited

U.S. PATENT DOCUMENTS 4,162,304  7/1979  Box et al. ................... 260/326.31

FOREIGN PATENT DOCUMENTS 2513855 10/1975  Fed. Rep. of Germany ...... 260/326.31
10914 of 1975  United Kingdom ............. 260/245.2 T

OTHER PUBLICATIONS

Hood et al.; The Jour. of Antibiotics, vol. XXXII, No. 4, pp. 295-304 (1979).
Brown et al.; J.C.S. Chem. Comm. (1977), pp. 523-525.
Corbett et al.; J.C.S. Chem. Comm. (1977), pp. 953-954.
Albers-Schönberg et al., J.A.C.S., vol. 100, pp. 6491-6499 (9-27-78).
Derwent Abstract/BE 839,324, 3/15/75.

*Primary Examiner*—Mary C. Lee
*Attorney, Agent, or Firm*—Hesna J. Pfeiffer; James A. Arno; Julian S. Levitt

[57] ABSTRACT

Disclosed are O-, N- and substituted carboxyl derivatives of the antibiotic thienamycin, which has the following structure:

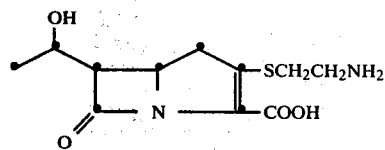

Such derivatives are useful as antibiotics. Also disclosed are processes for the preparation of such derivatives, pharmaceutical compositions comprising such derivatives, and methods of treatment comprising administering such derivatives and compositions when an antibiotic effect is indicated.

2 Claims, No Drawings

O-, N- AND CARBOXYL DERIVATIVES OF THIENAMYCIN

BACKGROUND OF THE INVENTION

This is a continuation-in-part of co-pending U.S. Pat. application Ser. No. 733,652, filed Oct. 18, 1976, which in turn is a continuation-in-part of co-pending U.S. Pat. application Ser. No. 634,294, filed Nov. 21, 1975, both now abandoned.

This invention relates to derivatives of the new antibiotic thienamycin. More particularly, the invention relates to certain N-, O- and carboxyl derivatives of thienamycin. Such derivatives are useful as antibiotics. This invention also relates to processes for the preparation of such compounds, pharmaceutical compositions comprising such compounds, and methods of treatment comprising administering such compounds and compositions when an antibiotic effect is indicated.

Thienamycin (I), is disclosed and claimed in co-pending, commonly assigned U.S. Pat. application Ser. No. 526,992, filed Nov. 25, 1974 (now U.S. Pat. No. 3,950,357, issued Apr. 13, 1976), which patent is incorporated herein by reference since thienamycin may serve as a starting material for the compounds of the present invention:

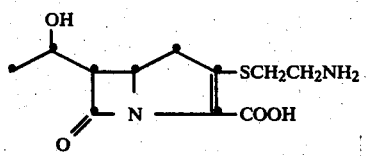
I

Thienamycin and all of its isomers (in pure form and as mixtures) are also obtainable by the total synthesis disclosed and claimed in co-pending, commonly assigned U.S. Pat. application Ser. No. 833,210 (Sept. 15, 1977), now abandoned. This application is incorporated herein by reference to the extent that it makes available all isomers of I as starting materials in the preparation of the compounds of the present invention.

Another convenient starting material is the N-acylated, carboxyl derivative of Thienamycin (Ia) which is disclosed and claimed in co-pending, concurrently filed U.S. Pat. application Ser. No. 634,295 filed Nov. 21, 1975 and in its continuation-in-part U.S. Pat. application Ser. No. 733,613, filed concurrently with the present application both now abandoned (Merck & Co., Inc. Attorney's Docket Number 15813IA):

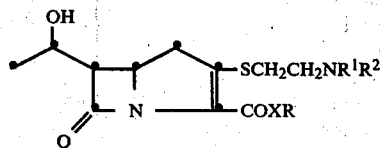
Ia wherein X, R, R¹ and R² are defined below. These applications are incorporated herein by reference as they describe useful starting materials.

The fully derivatized (i.e., N-, O- and carboxyl derivatives) thienamycin compounds of the present invention may be depicted by the following generic structural formula:

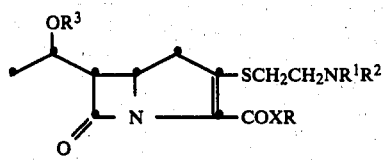
II or, more conveniently, by the symbol

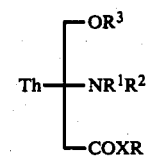
II wherein: "Th" symbolizes the bicyclic nucleus of thienamycin and the OH, amino, and carboxyl groups of thienamycin are illustrated; $R^1$ and $R^2$ are independently selected from the group consisting of hydrogen or an acyl group. Preferred compounds are those wherein $R^1$ is hydrogen and $R^2$ is acyl. The term "acyl" is by definition inclusive of the alkanoyls including derivatives and analogues thereof such as thio analogues wherein the carbonyl oxygen is replaced by sulphur, diacyl radicals wherein $R^1$ and $R^2$ are joined together; as well as the sulphur and phosphorous acyl analogues such as substituted sulfonyl-, sulfinyl- and sulfenyl-radicals and substituted P (III and V) radicals such as the substituted phosphorous-, phosphoric-, phosphonous- and phosphonic- radicals, respectively. Such acyl radicals of the present invention are further defined below; X is oxygen, sulphur or NR' (R'=H or R); and R is, inter alia, representatively selected from the group consisting of hydrogen, conventional blocking groups such as trialkylsilyl, acyl and the pharmaceutically acceptable salt, ester and amide moieties known in the bicyclic β-lactam antibiotic art; the definition of R is given in greater detail below; $R^3$ is 1.) acyl (generically the group $OR^3$ is classifiable as an ester); or 2.) $R^3$ is selected from alkyl, aryl, aralkyl and the like (such that the group $R^3$ is generically classifiable as an ether). The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl- radicals, and substituted P (III and V) radicals such as substituted phosphorous-, phosphoric-, phosphonous- and phosphonic- radicals, respectively. Such acyl radicals of the present invention are further defined below, as are the radicals (2., above) which constitute the ether embodiments of the present invention.

There is a continuing need for new antibiotics. For unfortunately there is no static effectiveness of a given antibiotic because continued wide scale usage of any such antibiotic selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure of the antibiotic thienamycin but which are characterized as the O-, N- and carboxyl-derivatives thereof. These antibiotics are active against a broad range of pathogens which representatively include both gram positive bacteria such as *S. aureus, B. subtilis,* and *Strept. pyogenes* and gram negative bacteria such as *E. coli,* and Salmonella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (II) are conveniently and preferably prepared in the following sequence: first thienamycin (I) is N-acylated to form the N-acyl intermediate (1) which is esterified to form the carboxyl derivative (2); derivatization of 2 provides II:

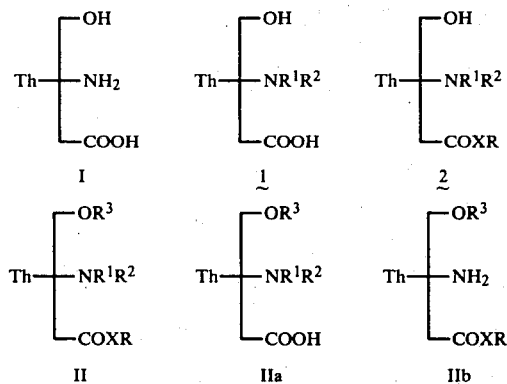

wherein all symbolism is as previously defined. Species of the present invention IIa are obtained when X is oxygen and R is an easily removable blocking group. Similarly when $R^1$ and $R^2$ are hydrogen or an easily removable N-blocking group, species IIb are obtained by selective deblocking.

It should be noted that the carboxyl group may, when desired, be derivatized first—prior to derivatization of the amino group.

The above preparation is described in greater detail below.

In the generic representation of the compounds of the present invention (II, above), the acyl radical represented by either $R^1$ or $R^2$ can, inter alia, be substituted or unsubstituted aliphatic, aromatic or heterocyclic, araliphatic or heterocylylaliphatic carboxylic acid radical, a substituted or unsubstituted carbamyl radical or a carbothioic acid radical. One group of acyl radicals can be represented by the general formula:

wherein X is O or S and R" represents hydrogen; amino; substituted amino such as alkyl- and dialkylamino wherein the alkyl radical comprises 1 to about 6 carbon atoms; substituted or unsubstituted; straight or branched chain alkyl wherein the alkyl radical comprises 1 to about 6 carbon atoms; mercapto such as alkylthio, typically comprising 1 to 6 carbon atoms; arylthio; typically comprising 6 to 10 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4–10 atoms and the hetero atom or atoms are selected from O,N and S; such above-listed groups can be unsubstituted or can be substituted by radicals such as OH, SH, SR (R is loweralkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing four radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, $\beta,\beta$-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-iosxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotrizolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)-methyl, 2- or 3-(5-methylthienyl)methyl, 2- or 3-(methoxythienyl)-methyl, 2- or 3-(4-chlorothienyl)-methyl,2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl)methyl, 2-furylmethyl, 2-(5-nitrofuryl)-methyl, 3-furylmethyl, 2-theinylmethyl, 3-thienylmethyl, tetrazolylmethyl benzamidinomethyl and cyclohexylamidinomethyl The acyl group can also be a radical of the formula:

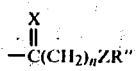

wherein X is O or S and n is 0–4, Z represents oxygen, sulfur, carbonyl or nitrogen and R'' is defined as above. Representative members of the substituent

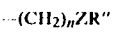

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

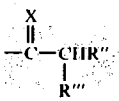

wherein R'' is defined as above and R''' is a radical such as amino, hydroxy, azido, carbamoyl, guanidino, amidino, acyloxy, halo, such as Cl, F, Br, I, sulfamino, tetrazolyl, sulfo, carboxy, carbalkoxy, phosphono and the like. Representative members of the substituent

that might be mentioned are α-aminobenzyl, α-amino-(2-thienyl)methyl, α-methylamino)benzyl, α-aminomethylmercaptopropyl, α-amino-3- or 4-chlorobenzyl, α-amino-3-or 4-hydroxybenzyl, α-amino-2,4-dichlorobenzyl, α-amino-3,4-dichlorobenzyl, D( )-α-hydroxybenzyl, α-carboxybenzyl, α-amino-(3-thienyl)methyl D-(−)-α-amino-3-chloro-4-hydroxybenzyl, α-amino(-cyclohexyl)methyl, α-(5-tetrazolyl)-benzyl, 2-thienylcarboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(−)-2-thienyl-guanidinomethyl, D(−)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl, 2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono. Further acyl radicals of interest in this class when X=oxygen are:

wherein $R^3$ and $R^4$ are as defined below. $R^3$ represents hydrogen, halo, such as chloro, fluoro, bromo, iodo, amino, guanidino, phosphono, hydroxy, tetrazolyl, carboxy, sulfo, or sulfamino and $R^4$ represents phenyl, substituted phenyl, a mono- or bicyclic heterocyclyl containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1–6 carbon atoms, heterocyclic or substituted heterocyclic thio groups; or cyano. The substituents on the moieties, $R^3$ and $R^4$, can be halo, carboxymethyl, guanidino, guanidinomethyl, carboxamidomethyl, aminoethyl, nitro, methoxy or methyl. When $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen hetero atom such as tetrazolyl, thienyl, furyl and phenyl, the following acyl radicals are representative: phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-gaunidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolyl-acetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

The acyl substituent $R^1$ and $R^2$ may also be selected from sulphur (1) and phosphorous (2) radicals:

wherein with respect to (1), m and n are integers selected from 0 or 1, and $Y = O^\ominus M^\oplus$, $-N(R'')_2$, and R'';

wherein M⊕ is selected from hydrogen alkali metal cations and organic bases; and R″ is as defined above, e.g., alkyl, alkenyl, aryl and heteroaryl. With respect to (2) X=O or S; n=0 or 1; and Y′ and Y″ are selected from the group consisting of O⊖M⊕, —N(R″)$_2$, R″ and ZR″ wherein all symbolism is as defined above, e.g., R″ and ZR″ are representatively: alkyl, alkenyl, aryl, heteroaryloxy; Y′ and Y″, including R″ moieties, can be joined together to form cyclic ester, ester- amide and amide functions. Illustrative examples of (1) are N-(methylsulphonyl)thienamycin, N-(o-nitrophenylsulphonyl)thienamycin, N-(p-chlorophenylsulphinyl)thienamycin, N-(o-nitrophenylsulphenyl)thienamycin, N-sulphamoylthienamycin, N-dimethylsulphamoylthienamycin and thienamycin N-sulphonic acid sodium salt. Illustrative examples of (2) are N-(dimethoxyphosphino)thienamycin, N-(dibenzyloxyphosphino)thienamycin, N-(dihydroxyphosphino)thienamycin disodium salt, N-(dimethoxyphosphinyl)thienamycin, N-(dimethoxyphosphinothioyl)thienamycin, N-(dibenzyloxyphosphinyl)-thienamycin, N-(dihydroxyphosphinyl)thienamycin disodium salt.

An acyl class of particular interest is those acyl radicals, R$^1$ and R$^2$ of Structure II, above, which are selected from the group consisting of conventionally known N-acyl blocking or protective groups such as carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as triloweralkylsilyl, for example, trimethylsilyl and t-butyldimethylsilyl are also of interest.

The following radicals, according to the foregoing definition of acyl (radicals R$^1$ and R$^2$ of Structure II, above), are preferred: formyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)amino propionyl, N,N,N-triethylaminoacetyl, pyridiniumacetyl, guanylthioacetyl, guanidinoacetyl, 3-guanidinopropionyl, N$^3$-methylguanidinopropionyl, hydroxyacetyl, 3-hydroxypropionyl, acryloyl, propynoyl, malonyl, phenoxycarbonyl, amidinoacetyl, acetamidinoacetyl, amidinopropionyl, acetamidinopropionyl, guanylureidoacetyl, guanylcarbamoyl, carboxymethylaminoacetyl, sulfoacetylaminoacetyl, phosphonoacetylaminoacetyl, N$^3$-dimethylaminoacetamidinopropionyl, ureidocarbonyl, dimethylaminoguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, o-aminobenzoyl,

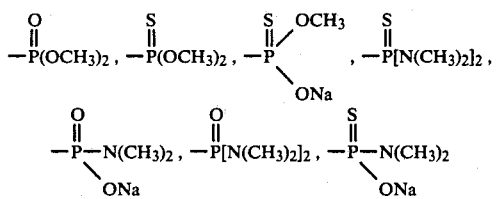

An especially preferred class of acyl radicals (R$^1$ and R$^2$ of structure II, above) are terminally substituted acyls wherein the substituent is a basic group such as substituted and unsubstituted: amino, amidino, guanidino, guanyl and nitrogen-containing mono- and bicyclic heterocycles (aromatic and non-aromatic) wherein the hetero atom or atoms, in addition to nitrogen, are selected from oxygen and sulphur. Such preferred substituted acyls may be represented by the following formula:

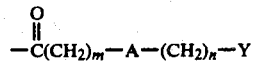

wherein m, and n are integers selected from 0 to 5; A is O, NR′ (R′ is hydrogen or loweralkyl having 1–6 carbon atoms), S or A represents a single bond; and Y is selected from the following group:

(1.) amino or substituted amino:
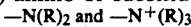
wherein the values for R are independently selected from: hydrogen; N(R′)$_2$ (R′ is hydrogen or loweralkyl having 1–6 carbon atoms); loweralkyl and loweralkoxy having from 1 to 6 carbon atoms; loweralkoxyloweralkyl wherein the alkoxyl moiety comprises 1 to 6 carbon atoms and the alkyl moiety comprises 2–6 carbon atoms; cycloalkyl and cycloalkylalkyl wherein the cycloalkyl moiety comprises 3–6 carbon atoms and the alkyl moiety comprises 1–3 carbon atoms; two R groups may be joined together with the N atom to which they are attached to form a ring having 3–6 atoms.

(2.) amidino and substituted amidino:

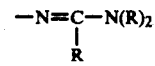

wherein the value of R is independently selected from the group consisting of: hydrogen; N(R′)$_2$ (R′ is hydrogen or loweralkyl having 1–6 carbon atoms); loweralkyl and loweralkoxyl having from 1 to 6 carbon atoms; loweralkoxyloweralkyl wherein the alkoxyl moiety comprises 1 to 6 carbon atoms and the alkyl moiety comprises 2 to 6 carbon atoms (when the loweralkoxyloweralkyl radical is attached to carbon the alkyl moiety comprises 1 to 6 carbon atoms); cycloalkyl and cycloalkylalkyl wherein the alkyl moiety comprises 1 to 3 carbon atoms; two R groups may be joined together with the atoms to which they are attached to form a ring having 3 to 6 atoms;

(3.) guanidino and substituted guanidino:

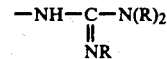

wherein R is as defined in 2. (above).

(4.) guanyl and substituted guanyl:

wherein R is as defined in 2. (above).

(5.) nitrogen-containing mono- and bicyclic heterocycles (aromatic and non-aromatic) having 4 to 10 nuclear atoms wherein the hetero atom or atoms, in addition to nitrogen, are selected from oxygen and sulphur. Such heterocycles are representatively illustrated by the following list of radicals (R' is H or loweralkyl having 1-6 carbon atom):

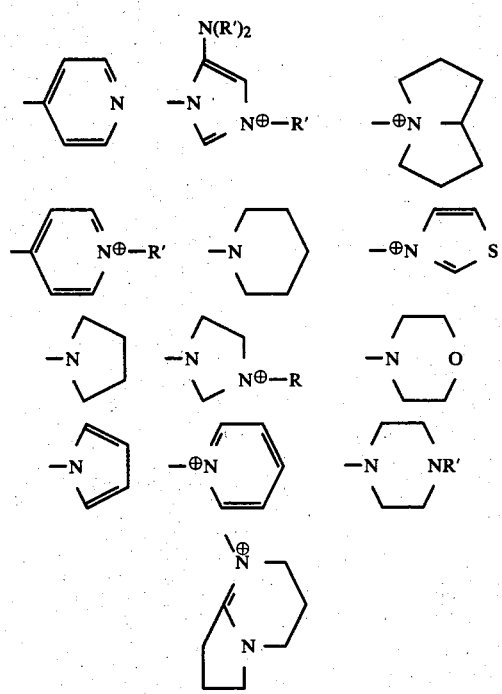

The following specific acyl radicals falling within this class are additionally representative and are preferred:

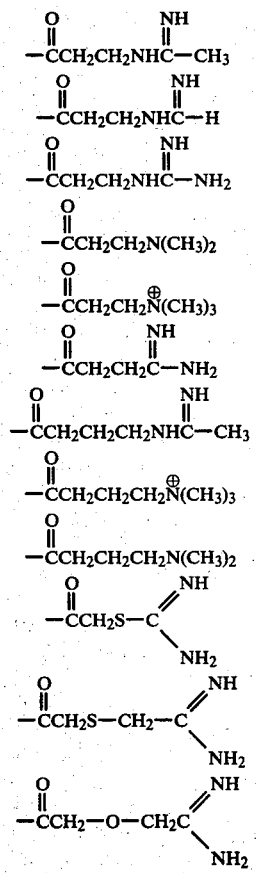

However, it is to be understood that any acyl radical may be employed in the practice of the invention and is to be considered within the scope of the invention.

The N-acylated intermediate (1, above) is prepared by treating thienamycin (I) with an acylating agent, for example, an acyl halide or acyl anhydride such as an aliphatic, aromatic, heterocyclic, araliphatic or heterocyclic aliphatic carboxylic acid halide or anhydride. Other acylating agents may also be employed, for example, mixed carboxylic acid anhydrides and particularly lower alkyl esters of mixed carboxylic-carbonic anhydrides; also, carboxylic acids in the presence of a carbodiimide such as 1,3-dicyclohexylcarbodiimide, and an activated ester of a carboxylic acid such as p-nitrophenyl ester.

The N-acylated thienamycin starting material is fully described in co-pending, concurrently filed U.S. Pat. application Ser. No. 634,291 filed Nov. 21, 1975 and in its continuation-in-part U.S. Pat. application Ser. No. 733,653, filed concurrently with the present application both now abandoned, (Merck & Co., Inc. Attorney's Docket Number 15775IA). These applications are incorporated herein by reference.

The acylation reaction may be conducted at a temperature in the range of from about $-20°$ to about $100°$ C. but is preferably conducted at a temperature in the range of from $-8°$ C. to $25°$ C. Any solvent in which the reactants are soluble and substantially inert may be employed, for example, polar solvents such as water, alcohols and polar organic solvents in general such as dimethylformamide (DMF) hexamethylphosphoramide (HMPA), acetone, dioxane, tetrahydrofuran (THF), acetonitrile, heterocyclic amines such as pyridine, ethylacetate, aqueous mixtures of the above, as well as halogenated solvents such as methylene chloride and chloroform. The reaction is conducted for a period of time of from about five minutes to a maximum of three hours, but in general, a reaction time of about 0.5 to about one hour is sufficient. The following equation illustrates this process employing a carboxylic acid halide; however, it is to be understood that by substituting a carboxylic acid anhydride or other functionally equivalent acylating agent similar products may be obtained.

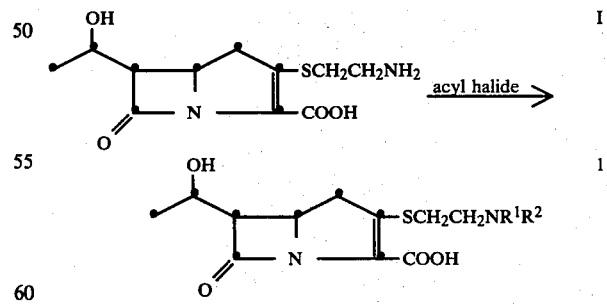

Generally when the above-described acylating reaction employs an acid halide (suitable halides are chloro, iodo, or bromo) or anhydride the reaction is conducted in water or an aqueous mixture of a polar organic solvent such as acetone, dioxane, THF, DMF, acetonitrile or the like in the presence of a suitable acceptor base such as $NaHCO_3$, MgO, NaOH, $K_2HPO_4$ and the like.

In carrying out the reactions described herein it is generally not necessary to protect the 2-carboxy group or the 1'-hydroxy group; however, in cases where the acylating reagent is exceedingly water sensitive it is sometimes advantageous to perform the acylation in a non aqueous solvent system. Triorganosilyl (or tin) derivatives of thienamycin are suitable for this purpose. Silylation of thienamycin proceeds rapidly to give the tris-triorganosilyl derivative, for example tris-trimethylsilyl thienamycin Th(TMS)$_3$:

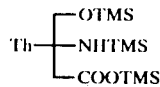

Such derivatives, which are readily soluble in organic solvents, are conveniently prepared by treating thienamycin with an excess of hexamethyldisilazane and a stoichiometric amount of trimethylchlorosilane at 25° C. with vigorous stirring under a N$_2$ atmosphere. The resulting NH$_4$Cl is removed by centrifugation and the solvent is removed by evaporation to provide the desired silyl derivative.

In the generic representation of the compounds of the present invention (II, above), the radical represented by —COXR, is, inter alia, —COOH (X is oxygen and R is hydrogen) and all radicals known to be effective as pharmaceutically acceptable ester, anhydride (R is acyl) and amide radicals in the bicyclic β-lactam antibiotic art, such as the cephalosporins and penicillins and the nuclear analogues thereof.

Suitable radicals (R) include conventional protecting or carboxyl blocking groups. Such blocking groups are employed in the preparation of species IIa, above. The term "blocking group" as utilized herein is employed in the same manner and in accordance with the teaching of U.S. Pat. No. 3,697,515, which is incorporated herein by reference. Pharmaceutically acceptable thienamycin derivatives of the present invention falling in this class are given below. Suitable blocking esters thus include those selected from the following list which is representative and not intended to be an exhaustive list of possible ester groups, wherein X=O and R is given:

(i) R=CR$^2$R$^b$R$^c$ wherein at least one of R$^a$, R$^b$ and R$^c$ is an electron-donor, e.g., p-methoxyphenyl, 2,4,6-trimethylphenyl, 9-anthryl, methoxy, CH$_2$SCH$_3$, tetrahydrofur-2-yl, tetrahydropyran-2-yl or fur-2-yl. The remaining R$^a$, R$^b$ and R$^c$ groups may be hydrogen or organic substituting groups. Suitable ester groups of this type include p-methoxybenzyloxycarbonyl and 2,4,6-trimethylbenzyloxycarbonyl.

(ii) R=CR$^a$R$^b$R$^c$ wherein at least one of R$^a$, R$^b$ and R$^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniummethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) R=CR$^a$R$^b$R$^c$ wherein at least two of R$^a$, R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, t-amyloxycarbonyl, diphenylmethoxycarbonyl and triphenylmethoxycarbonyl.

(iv) R=R$^d$, wherein R$^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula:

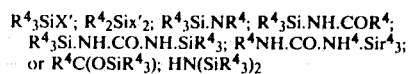

wherein X' is a halogen such as chloro or bromo and the various groups R$^4$, which can be the same or different, represent hydrogen atoms or alkyl, e.g., methyl, ethyl, n-propyl, iso-propyl; aryl, e.g., phenyl; or aralkyl, e.g., benzyl groups.

More generally stated, pharmaceutically acceptable carboxyl derivatives of the present invention are those derived by reacting N-acylated thienamycin (1) with alcohols, phenols, mercaptans, thiophenols, acylating reagents and the like which yield compounds (2, above) which are then derivatized to establish the R$^3$ group of the compounds of the present invention (II, above).

For example, esters and amides of interest are the compounds of the formula II (above) having the following group at the 2-position: —COXR wherein X is oxygen, sulfur or NR' (R' is as defined above), and R is alkyl having 1–10 carbon atoms, straight or branched, such as methyl, ethyl, t-butyl, pentyl, decyl and the like; carbonylmethyl including phenacyl, p-bromophenacyl, p-t-butylphenacyl, acetoxyacetylmethyl, pivaloxyacetylmethyl, carboxymethyl, and its alkyl and aryl esters, α-carboxy-α-isopropyl; aminoalkyl including 2-methylaminoethyl, 2-diethylaminoethyl, 2-acetamidoethyl, phthalimidomethyl, succinimidomethyl; alkoxyalkyl wherein the alkoxy portion has 1–10 and preferably 1–6 carbon atoms, but can be branched, straight or cyclic, and the alkyl portion has 1–6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy portion is straight or branched and has 1–6 carbon atoms and the alkyl portion has 1–6 carbon atoms, such as acetoxymethyl, pivaloyloxymethyl, acetoxyethyl, propionyloxyethyl, acetoxypropyl, and the like; haloalkyl wherein halo is chloro, bromo, fluoro, or iodo, and the alkyl portion is straight or branched having 1–6 carbon atoms, e.g., 2,2,2-trichloroethyl, trifluoroethyl, 2-bromopropyl, diiodomethyl, 2-chloroethyl, 2-bromoethyl, and the like; alkenyl having 1–10 carbon atoms, either straight or branched, e.g., allyl, 2-propenyl, 3-butenyl, 4-butenyl, 4-pentenyl, 2-butenyl, 3-pentenyl, 3-methyl-3-butenyl, metallyl, 1,4-cyclohexadien-1-yl-methyl, and the like alkynyl having 1–10 carbon atoms, either straight or branched, e.g., 3-pentynyl, propargyl, ethynyl, 3-butyn-1-yl, and the like; alkanoyl, either straight or branched, having 1–10 carbon atoms, such as pivaloyl, acetyl, propionyl, and the like; aralkyl or heteroaralkyl wherein alkyl has 1–3 carbon atoms, and hetero means 1–4 hetero atoms being selected from the group consisting of O, S, or N, such as benzyl, benzhydryl, and substituted benzyl, benzhydryl, or e.g., benzyl or benzhydryl substituted with 1–3 substituents such as benzyl, phenoxy, halo, loweralkyl, loweralkanoyloxy of 1–5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloyloxybenzyl, m-pivaloyloxybenzyl, p-isopropoxybenzyl, p-t-butoxybenzyl, as well as cyclic analogues thereof, 2,2-dimethyl-5-coumaranmethyl, 5-indanylmethyl, p-trimethylsilylbenzyl, 3,5-bis-t-butoxy-4-hydroxybenzyl; 2-thienylmethyl, 2-furylmethyl, 3-t-butyl-5-isothiazolmethyl, 6-pivaloyloxy-3-pyridazinylethyl, 5-phenylthio-1-tetrazolylmethyl, or the like (the use of the terms lower alkyl or lower alkoxy in this context means 1–4 carbon atom chain); or phthalidyl; or phenylethyl, 2-(p-methylphenyl) ethyl, and the arylthioalkyl analogues, aryloxyalkyl wherein aryl is preferably a phenyl ring having 0–3 substituents, preferably 0 or 1 substituents in the ortho or para positions and alkyl is 1–6 carbon atoms, e.g., (4-methoxy)-phenoxymethyl, phenoxymethyl, (4-chloro)phenoxymethyl, (4-nitro)phenoxymethyl, (4-benzyloxy)-phenoxymethyl, (4-methyl)phenoxymethyl, (4-benzyloxy)phenoxymethyl, (4-methyl)phenoxymethyl, (2-methoxy)phenoxymethyl, (1-phenoxy)-ethyl, (4-amino)phenoxymethyl, (4-methoxy)phenylthiomethyl, (4-chloro)phenylthiomethyl, phenylthioethyl; aryl wherein aryl is phenyl, 5-indanyl, or substituted phenyl having 0–3 substituents, preferably 0 or 1 substituent in the ortho or para position, e.g., (4-methyl)phenyl, (4-hydroxy)-phenyl, (4-t-butyl)phenyl, p-nitrophenyl, 3,5-dinitrophenyl or p-carboxyphenyl, the latter having either the free acid or the sodium salt form; aralkenyl wherein aryl is phenyl and alkenyl has 1–6 carbon atoms, such as 3-phenyl-2-propenyl; aralkoxyalkyl wherein aralkoxy is benzyloxy, and alkyl has 1–3 carbon atoms, such as benzyloxymethyl, (4-nitro)benzyloxymethyl, (4-chloro)benzyloxymethyl; alkylthioalkyl wherein the alkylthio portion has 1–10 and preferably 1–6 carbon atoms, but can be branched, straight, or cyclic, and the alkyl portion has 1–6 carbon atoms, such as methylthioethyl, ethylthioethyl, cyclohexylthiomethyl, decylthiobutyl, methylthiopropyl, isopropylthioethyl, propylthioethyl, methylthiobutyl and the like; alkoxycarbonyloxymethyl, dialkylaminoacetoxymethyl, and alkanoylamidomethyl, wherein the alkyl moieties of the last three mentioned radicals each comprise 1–6 carbon atoms.

In addition to the esters (and thio esters) listed above, amides are also embraced by the present invention, i.e., wherein X is the

group. Representative of such amides, Th-CONR'R, are those wherein R' is selected from the group consisting of hydrogen, methyl, ethyl, phenyl, p-methoxyphenyl, benzyl, carboxymethyl, methylthioethyl, and heteroaryl; also embraced by —COXR are anhydrides wherein R is benzyloxycarbonyl, ethoxycarbonyl, benzoyl, and pivaloyl.

Particularly preferred esters are those wherein X is oxygen, sulphur or NR' (R' is hydrogen or lower alkyl having 1–6 carbon atoms) and R is aralkyl, aryloxyalkyl, aralkoxyalkyl, alkylthioalkyl, haloalkyl and alkenyl.

The most preferred compounds of the present invention are those wherein (relative to structure II, above) X is oxygen, and R is selected from the group consisting of: lower alkyl, lower alkenyl, such as methallyl, 3-methylbutenyl, 3-butenyl and the like; methylthio ethyl; benzyl and substituted benzyl, such as p-t-butylbenzyl, m-phenoxybenzyl, p-pivaloyloxybenzyl, p-nitrobenzyl and the like; pivaloyloxymethyl, 3-phthalidyl, acetoxymethyl, propionyloxymethyl, acetylthiomethyl, pivaloylthiomethyl, allyl, 4-pentenyl, 2-butenyl, 3-methyl-2-butenyl, phenacyl, acetoxyacetylmethyl, pivaloyacetylmethyl, diethylaminoethyl, dimethylaminoethyl, methoxymethyl, p-acetoxybenzyl, p-pivaloyloxybenzyl, p-isopropoxybenzyl, 5-indanylmethyl, 5-indanyl, benzyloxymethyl, ethylthioethyl, methylthiopropyl, methoxycarbonyloxymethyl, ethoxycarbonyloxymethyl, dimethylaminoacetoxymethyl, crotonolacton-3-yl, and acetamidomethyl.

The preferred N-blocking groups for the starting material Ia are: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenylsulfenyl, 2,2,2-trichloroethoxycarbonyl, bromo-t-butoxycarbonyl, phenoxyacetyl; non-acyl protective groups such as alkylidenes, for example, benzylidene, salicylidene and the like are also of interest.

As noted above, the intermediate starting material for the preparation of 2(above) is prepared according to the following scheme:

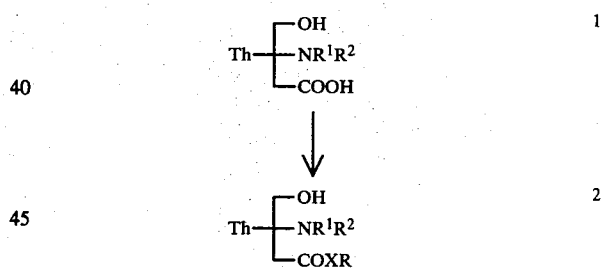

wherein all symbolism is as previously defined.

In general, the transformation (1→2) is accomplished by conventional procedures known in the art. Such procedures include:

(1) Reaction of 1 with a diazoalkane such as diazomethane, phenyldiazomethane, diphenyldiazomethane and the like, in a solvent such as dioxane, ethylacetate, acetonitrile and the like at a temperature of from 0° C. to reflux for from a few minutes to 2 hours.

(2) Reaction of an alkali metal salt of 1 with an activated alkyl halide such as methyl iodide, benzyl bromide, or m-phenoxybenzyl bromide, p-t-butylbenzyl bromide, pivaloyloxymethyl chloride, and the like. Suitable reaction conditions include solvents such as hexamethylphosphoramide and the like at a temperature of from 0° C. to 60° C. for from a few minutes to 4 hours.

(3) Reaction of 1 with an alcohol such as methanol, ethanol, benzyl alcohol, and the like. This reaction may be conducted in the presence of a carbodiimide condensing agent such as dicyclohexylcarbodiimide or the like. Suitable solvents, at a temperature of from 0° C. to reflux for from 15 minutes to 18 hours, include CHCl₃, CH₃CH, CH₂Cl₂ and the like.

(4) Reaction of an N-acylated acid anhydride of 1 prepared by reacting the free acid 1 with an acid chloride such as ethylchloroformate, benzylchloroformate and the like, with an alcohol such as those listed in (3) under the same conditions of reaction as given above for (3). The anhydride is prepared by reacting 1 and the acid chloride in a solvent such as tetrahydrofuran (THF), CH₂Cl₂ and the like at a temperature of from 25° C. to reflux for from 15 minutes to 10 hours.

(5) Reaction of labile esters of 1 or thienamycin such as the trimethylsilyl ester, dimethyl-t-butylsilyl ester or the like with RX' wherein X' is halogen such as bromo and chloro and R is as defined, in a solvent such THF, CH₂Cl₂ and the like at a temperature of from 0° C. to reflux for from 15 minutes to 16 hours. For example according to the following scheme:

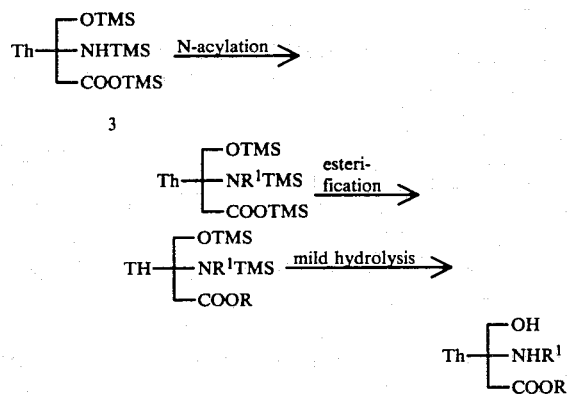

wherein TMS is triorganosilyl such as trimethylsilyl and all other symbolism is as previously defined.

The amides of the present invention are most conveniently prepared by reacting the acid anhydride of 2 (X=O, R=acyl) with ammonia or with the amine of choice, e.g., the alkyl-, dialkyl-, aralkyl- or hetero cyclic amines listed above.

The above-recited schemes of esterification are well-known in the related bicycic β-lactam antibiotic art and indeed in all of general organic synthesis and it is to be noted that there is no undue criticality of reaction parameters in the preparation of the N-acylated, carboxyl derivatives 2 useful as starting materials in the practice of the present invention.

Identification of $R^3$

In the generic representation of the present invention, Structure II (above), the radical $R^3$ is (1) acyl (generically the group —$OR^3$ is classifiable as an ester); or (2) $R^3$ is selected from alkyl, aryl, aralkyl, and the like such that the group —$OR^3$ is classifiable as an ether. For the ester embodiments (1), $R^3$ is selected from the above defined acyl radicals ($R^1$ and $R^2$). In the so-called ether embodiments (2) of the present invention, $R^3$ is selected from the above-identified acyl radicals wherein the carbonyl moiety,

or more generally

is deleted; thus $R^3$ is selected from the following radicals wherein all symbolism has been previously defined and p is an integer selected from 1 or 0.

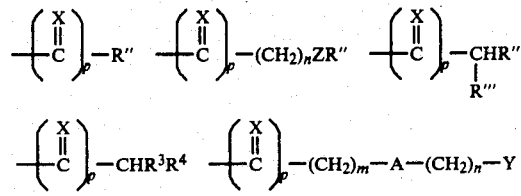

For the ether embodiments (2) as well as in the ester embodiments (1), the most preferred radicals, $R^3$, are those having a relatively low molecular weight, and which are hydrophilic. Thus, with respect to the ether embodiments (2), the following radicals are especially preferred: methoxymethy, hydroxyethyl, methoxyethyl, dimethylaminomethyl, dimethylaminoethyl, methylthioethyl, amidinoethyl, guanidinoethyl and the like. For the ester embodiments (1), the following radicals are representative and preferred: sulfo, phosphono, carbamoyl, methylsulfonyl, sulfamoyl, dimethylsulfamoyl, N-methyl carbamoyl, bromoacetyl, hydroxyacetyl, aminoacetyl, dimethylaminoacetyl, triethylammoniumacetyl, amidinoacetyl, guanidinoacetyl, methoxyacetyl, guanylacetyl, guanylthioacetyl, phosphamoyl, phosphonothioyl, thiocarbamoyl and the like.

In general, the compounds of the present invention are prepared by any of a variety of well-known esterification or etherification reactions (2→II) upon the secondary alcoholic group of 2. Such procedures (2→II) include:

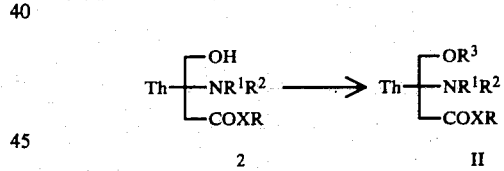

(1) For the preparation of ether embodiments of the present invention, the acid catalized reaction of 2 with a diazoalkane such as diazomethane, phenyldiazomethane, diphenyldiazomethane and the like in an inert solvent such as dioxane, tetrahydrofuran (THF), halohydrocarbons such as CH₂Cl₂, ethylacetate and the like in the presence of a catalytic amount of a strong acid or Lewis acid such as toluenesulfonic acid, trifluoroacetic acid, fluoboric acid, boron trifluoride and the like at a temperature of from −78° C. to 25° C. for from a few minutes to 2 hours.

(2) For the preparation of ether embodiments of the present invention, the reaction of 2 with an alkylating agent such as active halides for example methyliodide, benzylbromide, m-phenoxybenzylbromide and the like, alkyl sulphonates such as dimethylsulphate, diethylsulfate, methylfluorosulphonate and the like in the presence of a strong base capable of forming the alcoholate anion of 2. Suitable bases include alkali and alkaline earth metal oxides and hydrous oxides, alkali metal alkoxides such as potassium tertiary-butoxide, tertiary amines such as triethylamine, alkali metal alkyls and aryls such as phenyllithium, and alkali metal amides such as sodium amide. Suitable solvents include any inert anhydrous solvent such as t-butanol, dimethylformamide (DMF), THF, hexamethylphosphoramide (HMPA) dioxane and the like at a temperature of from −78° C. to 25° C., for from a few minutes to 4 hours.

(3) For the preparation of ester embodiments, of the present invention, the reaction of 2 with any of the above-listed acyl radicals in their acid form. This reaction may be conducted in the presence of a carbodiimide condensing agent such as dicyclohexylcarbodiimide or the like. Suitable solvents include any inert solvent such as $CHCl_3$, $CH_2Cl_2$, DMF, HMPA, acetone, dioxane and the like at a temperature of from 0° C. to 60° C. for from 15 minutes to 12 hours.

(4) For the preparation of ester embodiments of the present invention, the reaction of 2 with an acyl halide or an acid anhydride, wherein the acyl moiety is described above. Generally, when the above-described acylating reaction employs an acid halide (suitable halides are chloro, iodo, or bromo or acid anhydride) the reaction is conducted in an anhydrous organic solvent such as acetone, dioxane, methylenechloride chloroform, DMF, or the like in the presence of a suitable acceptor base such as $NaHCO_3$, MgO, triethylene, pyridine, and the like at a temperature of from 0° C. to 40° C. for from 1 to 4 hours.

Suitable acyl halides and anhydrides include: acetic anhydride, bromoacetic anhydride, propionic anhydride, benzoylchloride, phenylacetyl chloride, azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl ethyl carbonic anhydride, methylchloroformate, bis(p-nitrobenzyl)phosphorochloridate and the like.

(5) For the preparation of ester embodiments of the present invention, the reaction of 2 with a suitably substituted ketene or isocyanate such as ketene, dimethyl ketene, methylisocyanate, methylisothiocyanate, chlorosulfonyl isocyanate and the like. Suitable solvents include dioxane, tetrahydrofuran, chloroform and the like at a temperature of from −70° C. to 60° C. for from 15 minutes to 18 hours.

Embodiments of the present invention designated as IIb (above) are also preferred and are conveniently prepared by establishing either $R^1$ or $R^2$ as an easily removable N-blocking, or protecting, group; when embodiments IIb are desired the other N-substituent is hydrogen. The N-deblocking procedure for the preparation of IIb is accomplished by any of a variety of well-known procedures which include hydrolysis or hydrogenation; when hydrogenation is employed, suitable conditions involve a solvent such as a loweralkanoyl in the presence of a hydrogenation catalyst such as palladium, platinum or oxides thereof:

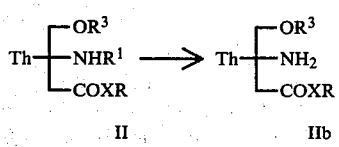

wherein all symbolism is as previously defined.

Suitable N-blocking groups for the preparation of IIb are: carbobenzyloxy, ring-substituted carbobenzyloxy such as o- and p-nitrocarbobenzyloxy, p-methoxycarbobenzyloxy, chloroacetyl, bromoacetyl, phenylacetyl, t-butoxycarbonyl, trifluoroacetyl, bromoethoxycarbonyl, 9-fluorenylmethoxycarbonyl, dichloroacetyl, o-nitrophenyl sulfenyl, 2,2,2-trichloroethoxycarbonyl, bromo-t-butoxycarbonyl, phenoxyacetyl; non-acyl protective groups such as triloweralkylsilyl, for example, trimethylsilyl and t-butyldimethylsilyl are also of interest.

Preferred N-blocking groups $R^1$ and $R^2$ are bromo-t-butoxycarbonyl and those wherein $R^1$ is hydrogen and $R^2$ is substituted or unsubstituted carbobenzyloxy radical:

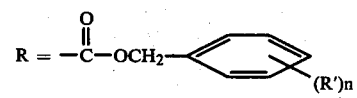

wherein n is 0–2 (n=O, R′=hydrogen) and R′ is lower alkoxy or nitro.

Embodiments of the present invention designated as IIa (above) are conveniently and preferably obtained when X is oxygen and R is a readily removable carboxyl protecting, or blocking, group (see above). Embodiments IIa are prepared by deblocking according to any of a variety of well-known procedures which include hydrolysis and hydrogenation; when the preferred carboxyl-blocking groups are employed (below), the preferred deblocking procedure is hydrogenation, wherein the intermediate species II, in a solvent such as a lower alkanoyl, is hydrogenated in the presence of a hydrogenation catalyst such as palladium, platinum or oxides thereof:

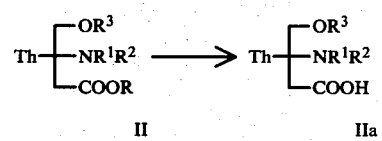

In this connection, it is noted that suitable "blocking groups" R include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms. For example, suitable "blocking groups" R include benzyl, phenacyl, p-nitrobenzyl, methoxymethyl, trichloroethyl, trimethylsilyl, tributyltin, p-methoxybenzyl, benzhydryl. These blocking groups are preferred since they are generally recognized as easily removable blocking groups in cephalosporin and penicillin art.

The preferred carboxyl blocking groups, R, are benzyl and substituted benzyl:

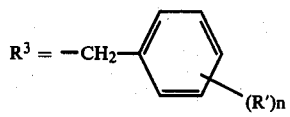

wherein n is 0–2 (n=O, R′=hydrogen) and R′ is lower alkoxy or nitro.

The compounds of the present invention are valuable antibiotics active against various gram-positive and gram-negative bacteria and, accordingly, find utility in human and veterinary medicine and in inanimate systems. The compounds of this invention can therefore be used as antibacterial drugs for treating infections caused by gram-positive and gram-negative bacteria, for example against *Staphylococcus aureus, Escherichia, coli, Klebsiella pneumoniae, Bacillus, substilis, Salmonella typhosa, Pseudomonas* and *Bacterium proteus*. The antibacterial compounds of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dentral equipment and as bacteridices in industrial applications, for example in waterbased paints and in the white water of paper mills to inhibit the growth of harmful bacteria.

The products of this invention may be used alone or in combinations as an active ingredient in any one of a variety of pharmaceutical preparations. These antibiotics and their corresponding pharmaceutically acceptable salt, ester and amide derivatives may be employed in capsule form or as tablets, powders or liquid solutions or as suspensions or elixirs. They may be administered orally, intravenously or intramuscularly. Such pharmaceutically acceptable forms are prepared according to procedures well-known in the art.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants for example, magnesium stearate, talc, polyethylene glycol, silica gel; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops. Topical applications may be formulated in hydrophobic or hydrophilic bases as ointments, creams, lotions, paints, or powders.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1 to about 99% of active material, the preferred range being from about 10–60%. The compositions will generally contain from about 15 mg. to about 1500 mg. of the active ingredient; however, in general, it is preferable to employ a dosage amount in the range of from about 250 mg. to 1000 mg. In parenteral administration the unit dosage is usually the pure compounds in a slightly acidified sterile water solution or as the form of a soluble powder intended for solution.

In the following Examples, which further illustrate but do not limit the product, process, compositional or method of treatment aspects of the present invention, the compounds of the present invention will be designated by the previously introduced symbol:

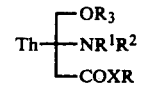

wherein the three functional groups are illustrated.

EXAMPLE 1

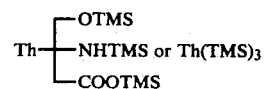

TMS=trimethylsilyl

Preparation of Silylated-Thienamycin

Thienamycin (80.0 mg.) is suspended in 40 ml. tetrahydrofuran (THF) and under a $N_2$ atmosphere and is concentrated to 10 ml., hexamethyldisilazane (1.0 ml.) and trimethychlorosilane (300 μl) is added. The mixture is reacted for 20 mins. at 25° C. with vigorous stirring.

The suspension is then centrifuged to remove ammonium chloride. The supernatant is evaporated to an oil under a nitrogen stream for future reaction.

EXAMPLE 2

Preparation of O-Methyl-N-(p-Nitrobenzyloxycarbonyl)-Thienamycin-p-Nitrobenzyl Ester

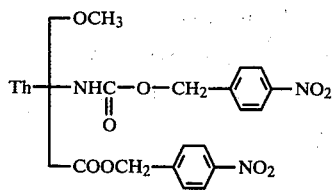

Step A

N-(p-Nitrobenzyloxycarbonylthienamycin Lithium Salt

To Thienamycin (220 mg. in 60 ml. water at 0° C.), is added successively, 679 mg. NaHCO$_3$, 60 ml. dioxane and then with stirring 1.1 equivalents p-nitrobenzylchloroformate over a period of 1.5 minutes. The mixture is allowed to react 10 minutes, and is then extracted three times with cold ethyl ether. Electrophoresis (0.05 M, pH 7, phosphate buffer, 50 V/cm., 20 minutes) shows no free Thienamycin present. The aq. extract is adjusted to pH 2.2 with 1 M H$_3$PO$_4$ solution and extracted three times with EtOAc. The EtOAc extract is dried over MgSO$_4$, filtered and reextracted 0.1 N LiOH, to pH 8.2. The final pH is adjusted to 7.0 with 1 M H$_3$PO$_4$ and the sample lyophilized. The yield is 205 mg. (54%).

Step B

N-(p-Nitrobenzyloxycarbonyl-Thienamycin-(p-nitrobenzyl Ester

A mixture of p-nitrobenzyloxycarbonyl-Thienamycin-lithium salt (295 mg.) and 0.4 g. of p-nitrobenzyl bromide in 3 ml. of hexamethyl phosphoramide is stirred for 3 hours at 25° C. The solution is diluted with 50 ml. of ethyl acetate and extracted successively with water (3 portions), pH 7 phosphate buffer and saturated sodium chloride solution. The organic phase is dired over magnesium sulfate and evaporated to 5 ml. causing the solvent to crystallize. The crystals are collected and washed with ethyl acetate, yield 160 mg. of N-p-nitrobenzyloxycarbonyl Thienamycin p-nitrobenzyl ester, M.P. 168°-170° C. NMR (CDCl$_3$) $\tau$1.35 (d), (J=6 Hz, CH$_3$), 4.0-4.3 and 2.8-3.5 (m); 5.16 (s), carbamate OCH$_2$; 5.24 (AB quartet J=14); 7.42 (d), 7.56 (d), 8.16 (d) J=9 Hz aromatic. IR 5.65$\mu$ (lactam C=O).

Step C

O-Methyl-N-(p-Nitrobenzyloxycarbonyl)-Thienamycin-(p-Nitrobenzyl Ester

To a solution of 135. mg. of N-p-nitrobenzloxycarbonyl-Thienamyin-(p-nitrobenzyl)ester in 50 ml. of methylene chloride at 0° C. is added with vigorous stirring 0.5 ml. of 0.006 M fluoboric acid in ether-methylene chloride (3:1) immediately followed by 10 ml. of a cooled solution of 0.6 M diazomethane in methylene chloride. The diazomethane is decolorized in one minute. The solution is extracted with 10 ml. of 0.1 N pH 7 phosphate buffer, dried and evaporated to a small volume. The solution is applied to two 8"×8" 1000$\mu$ silica gel plates which are developed with 3:1 ethylacetate-chloroform. The band at 3-4.5 cm yields 12 mg. of recovered starting material. The band at 6-8 cm yields 20 mg. of crystalline O-methyl N-p-nitrobenzyloxycarbonyl thienamycin p-nitrobenzylester. MP 172°-174° C. MS m/e 600 (M+), 568, 542, 500, 447, 389, 304 and 59.

EXAMPLE 3

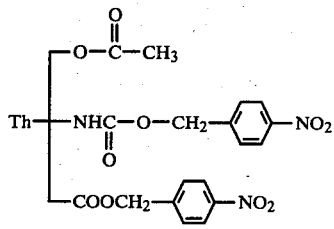

Preparation of O-Acetyl-N-(p-Nitrobenzyloxycarbonyl)-Thienamycin-(p-Nitrobenzyl)Ester To a solution of 50 mg. of p-nitrobenzyloxycarbonyl thienamycin p-nitrobenzylester in 0.5 ml. of pyridine is added 0.16 ml. of acetic anhydride. The mixture is allowed to react at room temperature for three hours, then pumped to dryness under vacuum. The solid residue is dissolved in chloroform and chromatographed on an 8"×8 1000$\mu$ silica gel plate in 3:1 ethylacetate-chloroform. The band at Rf 0.55 is isolated yielding 36 mg. of o-acetyl N-p-nitrobenzyloxycarbonyl Thienamycin p-nitrobenzyl ester, M.P. 172°-175° C. NMR (CDCl$_3$) $\delta$, 1.41, ((d) J=6 Hz CH$_3$), 2.04 ((s) COCH$_3$), 2.7-3.6 ((m) 4.14 (t of d) J=3 and 9 Hz), 5.17 (s) carbamyl C$\underline{H}_2$; 5.35 (AB quartet) J=14, Hz; 7.45 (d), 7.60 (d), 8.18 (d) J=9 Hz, aromatic H. Mass Spec M+ m/e 628.

EXAMPLE 4

Preparation of O-Acetyl-N-Azidoacetyl-Thienamycin-Benzyl Ester

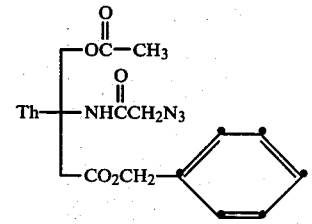

Step A

Preparation of N-Azidoacetyl-Thienamycin-Sodium (I) and Lithium (II) Salts

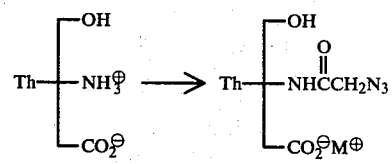

M=Na, Li (I) Thienamycin (48 mg., 0.18 mmol) is dissolved in 10 ml. cold water and is kept at 0°. To the solution is added sodium bicarbonate (147 mg., 17.6 mmol) and dioxane (10 ml.). Azidoacetyl chloride (60 mg., 0.50 mmol) is added to the solution during a period of 2 min. The reaction mixture is stirred for 15 min. then is neutralized to pH 7.0 with 30% phosphoric acid and is transferred into a separatory funnel. The solution is extracted with 2×50 ml. The aqueous layer is concentrated to 5 ml. and then is charged to a Dowex AG-50×8 (sodium form) ion exchange column monitored by UV. The desired fractions are combined and lyophilized to give 21 mg. of the product. The electrophoresis (50 V/cm., 20 min.) of the product in pH 7.0 phosphate buffer shows a single bio-active band which moves 40 mm. towards the anode. UV$\lambda_{max}^{H2O}$ 300 nm; NMR (100 MHz, D$_2$O): δ 1.26 (d, C$\underline{H}_3$CH); 2.92–3.43 (m, 3 CH$_2$ and C$_6$-$\underline{H}$), 4.01 (s, C$\underline{H}_2$N$_3$) and 4.20 ppm (m, C$_5$-$\underline{H}$ and C$_7$-$\underline{H}$).

II. Thienamycin (76.2 mg., 0.28 mmol.) is dissolved in 10 ml. of cold water and is kept at 0° C. To the solution is added 0.6 ml. of 1.0 N lithium hydroxide solution and 10 ml. dioxane. After stirring for 1 min., azidoacetyl chloride (33.6 mg., 0.28 mmol.) is added during a period of 2 min. The reaction mixture is stirred for additional 1 min. then is neutralized to pH 7.0 with 30% phosphoric acid. After extraction with ether, the aqueous solution is concentrated to 5 ml. and is charged to the Dowex AG-50×8 (lithium form) ion exchange column. The desired fractions are combined and lyophilized to give 38 mg. of the product UV $_{max}^{H2O}$ 300 nm.

Step B
Preparation of N-Azidoacetyl-Thienamycin-Benzyl Ester

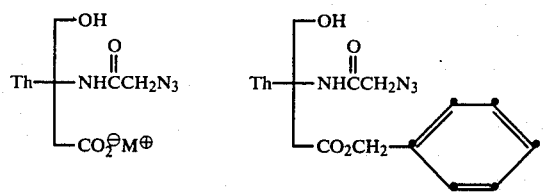

(a) N-Azidoacetyl-Thienamycin-lithium salt (3.0 mg.) is stirred with hexamethylphosphoramide (HMPA) (1.0 ml.) and benzyl bromide (30 mg., 0.21 mmol.) for 30 min. The reaction mixture is then diluted with ethyl acetate (5 ml.) and washed thoroughly with water. The organic layer is separated and dried over sodium sulfate. The product (2.0 mg.) is isolated by silica gel TLC (R$_f$=0.18 in ethyl acetate). IR (CHCl$_3$): 2125 (N$_3$), 1777 (β-lactam) and 1687 cm$^{-1}$ (ester and amide); NMR (CDCl$_3$, 100 MHz): 1.34 (d, C$\underline{H}_3$CH), 2.80–3.60 (m, 3CH$_2$ and C$_6$-H), 3.97 (s, C$\underline{H}_2$N$_3$), 4.21 (m, C$_5$-$\underline{H}$ and C$_7$-$\underline{H}$), 5.19 and 5.34 (d, C$\underline{H}_2$C$_6$H$_5$), 6.63 (m, N$\underline{H}$) and 7.32 (m, C$_6$H$_5$).

(b) N-Azidoacetyl-Thienamycin-sodium salt (30 mg., 0.08 mmol.) is stirred with HMPA (3 ml.) and benzyl bromide (120 mg., 0.70 mmol.) at room temperature for 30 min. The product (30 mg.) is isolated by the same procedure described above.

STEP C
Preparation of O-Acetyl-N-Azidoacetyl-Thienamycin-Benzyl Ester

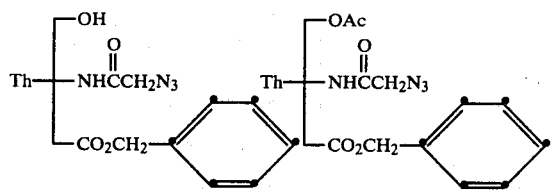

N-Azidoacetyl-Thienamycin-benzyl ester (30 mg., 0.067 mmol.) is dissolved in 0.5 ml. of pyridine. To the solution is added acetic anhydride (0.2 ml.). The mixture is kept at room temperature for 40 min. The solution is diluted with 1 ml. ethyl acetate and washed with ice-water. The organic layer is separated and dried over sodium sulfate. The desired product (10 mg.) is isolated by silica gel TLC (R$_f$=0.49 in ethyl acetate). IR (CHCl$_3$): 2121 (N$_3$), 1777 (β-lactam), 1738 (OAc), and 1683 cm$^{-1}$ (ester and amide): NMR (CDCl$_3$, 60 MHz): 1.38 (d, C$\underline{H}_3$CH), 2.05 (s, OAc), 3.96 (s, C$\underline{H}_2$N$_3$), 5.20 (s, C$\underline{H}_2$C$_6$H$_5$), and 7.40 ppm (m, C$_6$H$_5$).

EXAMPLE 5

Preparation of O-Acetyl-N-Glycyl-Thienamycin

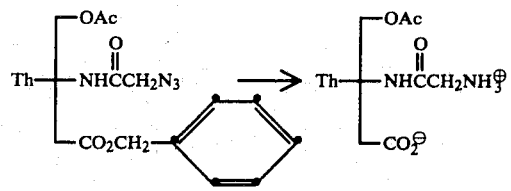

O-Acetyl-N-Azidoacetyl-Thienamycin-benzyl ester (5.0 mg., 0.006 mmol.) is dissolved in 0.3 ml. dioxane. The solution is added to the hydrogenation flask which containing 20 mg. of palladium (from palladium oxide) and 0.5 ml. 50% dioxane in water. The mixture is stirred for 10 min. then is filtered from the catalyst. After extraction with ether, the solution is lyophilized to give the desired product. Electrophoresis of the product in pH 7.0 buffer shows one bio-active band at the origin (50 V/cm., 20 min.).

EXAMPLE 6

Preparation of O-Acetyl-N-Azidoacetyl-Thienamycin-3-Methyl-2-Butene-1-yl Ester

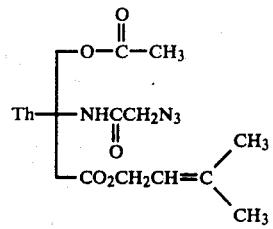

Step A
Preparation of N-Azidoacetyl-Thienamycin-3-Methyl-2-Butene-1-yl Ester

N-Azidoacetyl-Thienamycin-sodium salt (11.0 mg., 0.029 mmol.) is stirred with HMPA (1 ml.) and 1-bromo-3-methyl-2-butene (39 mg., 0.26 mmol.) at room temperature for 30 min. The mixture is then diluted with 10 ml. ethyl acetate and washed thoroughly with water. The desired product (10 mg.) is isolated by silica gel TLC (R$_f$=0.18 in ethyl acetate). IR (CHCl$_3$: 2121 (N$_3$), 1777 (β-lactam) and 1685 cm$^{-1}$ (ester and amide): NMR (CDCl$_3$, 100 MHz: 1.34 (d, C$\underline{H}_3$CH),

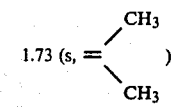

2.80–3.80 (m, 3C$\underline{H}_2$ and C$_6$-$\underline{H}$), 3.98 (s, C$\underline{H}_2$N$_3$), 4.20 (m, C$_5$-$\underline{H}$ and C$_7$-$\underline{H}$), 4.72 (d, C$\underline{H}_2$CH=), 5.40 (t, CH$_2$C$\underline{H}$=), and 6.70 (broad, N$\underline{H}$); Mass Spect. (E. I.): e/m 423 (molecular ion), 405 (M$^+$-H$_2$O), 395 (M$^+$-N$_2$), and 337 (M$^+$-86).

STEP B

Preparation of O-Acetyl-N-Azidoacetyl-Thienamycin-3-Methyl-2-Butene-1-yl Ester

N-Azidoacetyl-Thienamycin-3-methyl-2-butene-1-yl ester (5.0 mg.) is dissolved in pyridine (0.5 ml.). To the solution is added acetic anhydride (0.1 ml.). The mixture is kept at room temperature for 2 hours then is evaporated to dryness. The residue is worked up by silica gel TLC to give the desired product (R$_f$=0.52 in ethyl acetate). NMR (CDCl$_3$, 100 MHz): 1.38 (d, C$\underline{H}_3$CH),

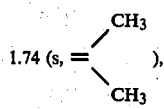

2.03 (s, OAc), 2.90–3.80 (m, 3C$\underline{H}_2$ and C$_6$-$\underline{H}$), 3.98 (s, C$\underline{H}_2$N$_3$), 4.20 (m, C$_5$-$\underline{H}$), 4.74 (d, C$\underline{H}_2$CH=), and 5.32 ppm (t, CH$_2$C$\underline{H}$=).

EXAMPLE 7

Preparation of O-Acetyl-N-Glycyl-Thienamycin-3-Methyl-2-Butene-1-yl Ester

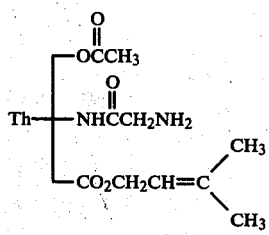

O-Acetyl-N-Azidoacetyl-Thienamycin-3-methyl-2-butene-1-yl ester (10 mg.) is dissolved in ethylacetate (1 ml.). This solution is added to the hydrogenation flask which containing 10 mg. of palladium (from palladium oxide) and 0.5 ml. 50% methanol in ethyl acetate. The mixture is stirred under 1 atm hydrogen at 25° C. for 1 hr. The mixture is filtered from the catalyst. The desired product is isolated by silica gel TLC (20% methanol/chloroform). Electrophoresis of the product at pH 7.0 buffer (50 V/cm., 20 min.) shows one bio-active band which moves toward cathode.

EXAMPLE 8

Preparation of N-(p-nitrobenzyloxycarbonyl)-Thienamycin p-t-butyl benzyl Ester

N-(p-nitrobenzyloxycarbonyl)Thienamycin Li salt, the product of Example 2, (205 mg) in 2 ml. hexamethylphosphoramide (HMPA) is treated for 2.5 hrs. with 0.1625 ml. p-t-butylbenzyl bromide. The starting material is insoluble in HMPA but goes into solution after 30 minutes.

The reaction mixture is diluted with ethyl acetate (EtOAc), washed successively with water, aqueous K$_2$HPO$_4$, water, saturated aqueous NaCl, dried over MgSO$_4$, filtered evaporated and subjected to preparative thin layer chromatography on silica gel; eluting with 1:2 CHCl$_3$: EtOAc. Yield 160 mg (58%), Rf 0.38, IR ($\mu$ film) 2.98 NH and OH 5.63, $\beta$-lactam, 5.86 broad ester and urethane; NMR ($\delta$, CDCl$_3$), 1.24 (s, CHCH$_3$, t-butyl), 2.59–3.27 (m, CH$_2$) 3.83–4.47 (m, CH $\beta$-lactam), 5.15 (s OC$_2$C$_6$H$_4$NO$_2$), 5.22 (s OCH$_2$C$_6$H$_4$ t-butyl (7.45 and 8.12 (AB quartet, J=8 Hz C$_6$H$_4$NO$_2$), C$_6$H$_4$ t-butyl).

EXAMPLE 9

Preparation of N-(p-Nitrobenzyloxycarbonyl)Thienamycin m-Phenoxybenzyl Ester

Following the procedure of Example 8, the title compound is prepared when an equivalent amount of m-phenoxybenzyl bromide is substituted for the p-t-butylbenzyl bromide of Example 8, Yield 11%, IR ($\mu$ film) 3.0 NH$_2$, and OH 5.63 $\beta$-lactam; 5.86 broad peak ester and urethane; nmr ($\delta$ CHCl$_3$) 1.33 (d CHC$\underline{H}_3$ J=6); 2.60–3.62 (m, CH$_2$), OCH$_2$C$_6$H$_4$OC$_6$H$_5$); 7.45 and 8.13 (AB quartet, J=8, C$_6$H$_4$NO$_2$); 7.26 (s C$_6$H$_4$OC$_6$H$_5$) M.S. m/e 589, 559, 547, 183.

EXAMPLE 10

Preparation of:
(1) N-(O-Formyl-D-mandeloyl Thienamycin p-t-butylbenzyl ester
(2) N-(O-Formyl)-D-mandeloyl Thienamycin m-phenoxybenzyl ester
(3) N-(D-Mandeloyl Thienamycin p-t-butylbenzyl ester
(4) N-D-Mandeloyl Thienamycin m-phenoxybenzyl ester
(5) N-Propionyl Thienamycin p-t-butylbenzyl ester
(6) N-Propionyl Thienamycin m-phenoxybenzyl ester
(7) N-Methoxyacetyl Thienamycin p-t-butylbenzyl ester
(8) N-Methoxyacetyl Thienamycin m-phenoxybenzyl ester.

Following the procedure of Examples 8 and 9, title compounds 1., 3., 5., 7 and 2., 4., 6., 8 are prepared respectively, when the appropriate N-acyl thienamycin starting materials (prepared in exact analogy to the above-illustrated N-acyl thienamycin) replace, in equivalent amount, the N-(p-nitrobenzyloxycarbonyl)thienamycin starting material of Examples 8 and 9, respectively.

EXAMPLE 11

Preparation of N-(p-Methoxybenzyloxycarbonyl)-thienamycin p-t-Butylbenzyl Ester

Step A: N-(p-methoxybenzyloxycarbonyl)thienamycin Sodium salt (I) and Lithium Salt (II)

To Thienamycin (20 mg.) in 5 ml. water at 0° C. is added 105 mg. NaHCO$_3$ (20 equivalents), 5 ml. dioxane, and then, dropwise with stirring over 1 min. ten equivalents of p-methoxybenzyl chloroformate. After 15 min. the pH is adjusted to 7.5 with 1 M H$_3$PO$_4$ and the solution extracted 3× with ether. The aqueous portion is then adjusted to pH 2.2 at 0° C. and extracted 3× with ethylacetate (EtOAc). The EtOAc is dried quickly with MgSO$_4$, filtered and extracted with a few ml. water containing 6.3 mg. NaHCO$_3$. The first extract, lyophilized, contains 172 ODU at 303 nm by UV analysis in H$_2$O at pH 7.0, which is 95% extinguished after treatment with hydroxlamine for one hour. The yield is 16 mg. Electrophoresis (50 v/cm., 20 min., pH 7 aqueous phosphate, 0.05 M) shows one spot by bioautograph, 4 cm towards the anode. NMR ($\delta$, D$_2$O); 1.49 (d, J=6 Hz C$\underline{H}_3$CH); 2.8–3.7 (m, CH$_2$); 3.99 (s, OMe); 4.0–4.6 (m, β-lactam CH); 4.92 (s, HDO); 5.20 (s, OCH₂); 7.13 (d, J=8 Hz C₆H₄).

The lithium salt II is made in the same way, but extracting the EtOAc solution with 0.1 N LiOH to pH 7.8 (instead of aqueous NaHCO₃), and lyophilizing. The spectral and electrophoretic properties of II are the same as those of I.

Step B: N-(p-methoxybenzyloxycarbonyl)thienamycin-p-t-benzyl ester

The lithium salt of Step A (37 mg.) in 0.4 ml. hexamethylphosphoramide (HMPA), is treated for 2 1/5 hours with 0.033 ml. p-t-butylbenzyl bromide. The lithium salt is insoluble in HMPA but goes into solution after 15 minutes reaction time.

The reaction mixture is diluted with EtOAc, washed successively with water twice, aqueous K₂HPO₄, water and brine, dried with MgSO₄, filtered, evaporated and subjected to preparative layer chromatography on silica gel, eluting with 1:2 CHCl₃-EtOAc, affording 47 mg. pure II, Rf=0.3. IR (μ, film): 3.0, NH; 5.63, β-lactam; 5.87 broad, ester and urethan. NMR (δ, CDCl₃): 1.21 (s Me and t-butyl); 2.6–3.6 (m, CH₂); 3.72 (s, OMe); 3.8–4.4 (m, β-lactam CH);

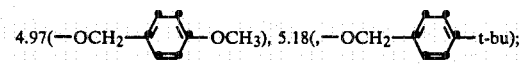

6.84 and 7.20 (AB quartet, C₆H₄OMe); 7.32 (s, C₆H₄-t-Bu). MS: 582, 538, 496.

EXAMPLE 12

Preparation of N-(p-methoxybenzyloxycarbonyl)thienamycin Benzhydryl Ester

To Thienamycin (23.5 mg.) in 5 ml. water is added successively 4 ml. dioxane, 62 mg. NaHCO₃, and then, in portions at 0° C. with stirring, 4 equivalents p-methoxybenzyl chloroformate over 4 minutes. After ten minutes total reaction time, the pH is adjusted to 7.0 with 1 M H₃PO₄ and the mixture extracted three times with ether. Electrophoresis of the aqueous portion (0.05 M pH 7 aqueous phosphate buffer, 50 V/cm, 20 minutes) shows 50% conversion to N-(p-methoxybenzyloxycarbonyl)thienamycin.

The aqueous solution is brought to pH 2.2 with 1 M H₃PO₄ at 0° C. and extracted 3× with EtOAc. The EtOAc solution is treated with 50 mg. diphenyldiazomethane, evaporated and taken up in CH₃CN. More diphenyldiazomethane is added to a persistent purple color. After 0.5 hour the solution is evaporated and chromatographed on silica gel, eluting with 1:2 CHCl₃-EtOAc, affording 10 mg. pure title compound Rf 0.25. IR (μ, film): 3.0, NH; 5.63, β-lactam; 5.85, 5.89, ester and urethan. NMR (δ, CDCl₃); 1.23 (s, OH); 1.30 (d, J=6 Hz, C$\underline{H}$₃CH); 2.6–3.6 (m, CH₂); 3.78 (s, OMe); 5.02 (s OCH₂); 3.8–4.4 (m, β-lactam CH); 6.9 and 7.35 (AB quartet, J=9 Hz, C₆H₄), 7.3s CHPh₂.

EXAMPLE 13

Preparation of N-(o-nitrobenzyloxycarbonyl)Thienamycin Benzyl Ester

Step A: N-(o-Nitrobenzyloxycarbonyl)thienamycin Sodium Salt

To Thienamycin (43 mg.) at 0° C. is added 10 ml. 1:1 tetrahydrofuran (THF:Water). The mixture is rapidly stirred while 102 mg. NaHCO₃ (10 equivalents) is added, and then, dropwise with stirring over 2 minutes, four equivalents of o-nitrobenzylchloroformate is added. After 30 minutes, the pH is adjusted to 7 with aqueous 25% H₃PO₄ and the solution extracted three times with ether. The aqueous layer is evaporated at 25° C., in vacuo and is then adjusted to pH 2.2 at 0° C. Solid NaCl is added, and the cold acidic solution is extracted 3× with cold EtOAc. The EtOAc extracts are combined and quickly back-washed with cold brine; dried with MgSO₄, filtered and back extracted with 10 ml. of water containing 1.75 equivalents of solid NaHCO₃. The extract is lyophilized in vacuo at 25° C. to provide the title compound.

Step B: N-(o-Nitrobenzyloxycarbonyl)Thienamycin Benzyl Ester

The product of Step A is 7.5 ml. EtOAc (from the pH 2.2 extraction) is treated with an excess of phenyldiazomethane (4 ml. of solution comprising 20 mg./ml. ether) at 4° C. for 2.3 hours. The mixture is concentrated to wet residue at 20° C. under reduced pressure. The desired compound is isolated by thin chromatography, EtOAc; ether (9:1) to afford 17.5 mg. of N-(o-Nitrobenzyloxycarbonyl)thienamycin benzyl ester.

EXAMPLE 14

Preparation of N-(o-Nitrobenzyloxycarbonyl)Thienamycin p-methoxy Benzyl Ester

To N-(o-Nitrobenzyloxycarbonyl)thienamycin (70 mg.) in 8 ml. of EtOAc is added 4 ml. of p-methoxyphenyldiazomethane (9 mg./ml. acetonitrile) at 4° C. The mixture is stirred for 1.5 hours at 4° C. and is then concentrated to a wet paste under reduced pressure at 20° C. The title compound (42 mg.) is isolated by thin layer chromatography on silica gel, eluting with EtOA:ether (9:1).

EXAMPLE 15

Preparation of N-(o-nitrobenzyloxycarbonyl)thienamycin p-Bromo-phenacyl Ester

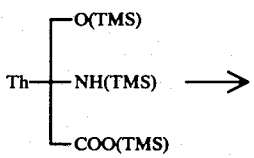

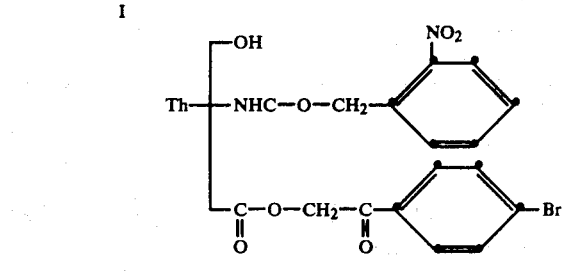

[wherein TMS=trimethylsilyl]

To Th (TMS)₃, I, (24 mg.), which is prepared according to Example 11, in 0.8 ml. dry THF is added 23 mg. o-nitrocarbobenzyloxy chloride, followed by 0.015 ml. of triethylamine. After vibro-mixing for 30 minutes at 25° C., the mixture is concentrated to a pasty residue in a stream of dry N₂, and is washed 3× with petroleum ether. The residue is suspended in 1 ml. of dry THF and p-bromophenacylbromide (14 mg.) is added followed by 0.03 ml. triethylamine. After vibro-mixing for 30 minutes at 25° C., the mixture is evaporated to dryness in vacuo at 20° C. The residue is dissolved in EtOAc (2 ml) and shaken with 0.3 ml. of pH 4 buffer for 5 minutes. The organic layer is dried over MgSO4, filtered, evaporated to a pasty residue and the desired product is isolated (44 mg) by preparative thin layer chromatography on silica gel, eluting with EtOAc:CHCl3 (7:3).

EXAMPLE 16

Preparation of N-(Trichloroethoxycarbonyl)thienamycin Benzyl Ester

Step A: N-(Trichloroethoxycarbonyl)Lithium Salt

To thienamycin (40 mg.) in 18 ml. 1:1 THF-H2O at 0° C. is added while stirring 225 mg. (15.2 equivalents) NaHCO3, and then, dropwise with stirring over 2 min., 1.8 equivalents of trichloroethylchloroformate dissolved in 0.6 ml. THF. After 6 minutes the pH is adjusted to 7.2 with aqueous 25% H3PO4 and the solution extracted with ether. The aqueous portion after removing any entrained ether in vacuo is then brought to pH 2.5 at 0° C. and extracted with cold EtOAc. The ethyl acetate extracts are combined, quickly backwashed with cold brine, dried with anhydrous MgSO4, filtered and back extracted with 0.01 m LiOH to pH 6.8. The aqueous extract is freed from any EtOAc in vacuo and lyophilized. The residual product contains 936 ODu (39.7%) by uv analysis at 302 nm which is 90% extinguished after treatment with hydroxylamine for one hour in 0.05 M phosphate buffer (pH 7). The yield is 32 mg. Electrophoresis (50 volts/cm. 20 min., pH 7 aq. phosphate 0.05 M) exhibits one zone by bioautograph (MB 108, staph. aureus)., 2.4 cm toward the anode. Liquid chromatography C18 Bondapak (Waters Assoc.) in aqueous 10% THF exhibits one main peak free of any unreacted Thienamycin.

Step B: N-(Trichloroethoxycarbonyl)thienamycin Benzyl Ester

The compound of Step A (32 mg.) in 2 ml. dry distilled DMF containing 7% HMPA (dry, pH 6.3), is treated with 0.015 ml. benzyl bromide for 2 hours at 15° C. (allowing the contents to warm up to 25° C. during the course of the reaction). The reaction mixture is diluted with EtOAc, washed successively with cold H2O, 1% aqueous NaHCO3, water and cold saturated aqueous NaCl, dried with MgSO4, filtered, evaporated and subjected to preparative thin layer chromatography on silica gel, eluting with 1% CH3CN in EtOAc to afford 10 mg. of the title compound, Rf=0.63; IR ($\mu$ CHCl3) 5.63, $\beta$-lactam; 5.78 and 5.88 broad ester and urethane. NMR ($\delta$ CDCl3) 1.35 (d, Me); 2.8–3.7 (m CH2); 3.51 and 4.27 (dd, J=6 Hz, $\beta$-lactam CH); 4.79 (s, OCH2CCl3) 5.42 s(OCH2C6H5); and 7.41 (m, C6H5).

EXAMPLE 17

Preparation of N-Bromoacetyl thienamycin Methyl and Benzyl Esters

Step A: N-Bromoacetyl thienamycin

To a cooled solution of thienamycin (28.8 mg.) and sodium bicarbonate (0.3 g.) in 10 ml. of water and 8 ml. of dioxane is added with stirring a solution of 0.25 g. of bromoacetic anhydride in 2 ml. dioxane over a period of 20 minutes. The pH is maintained at 8.0. The mixture is stirred for an additional 5 minutes then layered with 10 ml. of ether and the pH adjusted to 7 by the additional of 8% phosphoric acid. The ethereal layer is separated and the aqueous layer is extracted twice again with ether. The aqueous layer is evaporated under reduced pressure to 0.5 ml., diluted to 2 ml. with water and put on 50 ml. of XAD-2 resin. The column is eluted with water. The first 80 ml. is discarded, then the next 100 ml. is collected. The solvent is changed to 10% THF and an additional 100 ml. collected. The combined eluates are adjusted to pH 7, evaporated to 5 ml. under reduced pressure, then freeze-dried to give the sodium salt of N-bromoacetyl thienamycin in 60% yield. UV$\lambda_{max}$ 302 m$\mu$.

Step B: N-Bromoacetyl thienamycin Methyl and Benzyl Esters

An aqueous solution of the sodium salt is layered with ethyl acetate at 0° C. and adjusted to pH 2. The ethyl acetate phase is separated and the aqueous phase is extracted with ethyl acetate. The combined ethyl acetate solutions are dried over MgSO4 and then treated with a solution of diazomethane. The solvents are evaporated and the residue chromatographed on silica gel plate. R$_f$ 0.11 in 2:1 ethyl acetate-chloroform. m.p. 118°–120° C. Mass spectrum shows M+ at m/e 406 and significant fragments at m/e 362, 320, 183 and 164.

The corresponding benzyl ester is prepared in a similar way from phenyldiazonemethane. m.p. 142°–3° C.

Ir: 5.65$\mu$, 5.89$\mu$ and 6.1$\mu$. Mass spec. M+ m/e 482 also m/e 438, 396, 316, 259 and 164.

EXAMPLE 18

Preparation of N-(Guanylthioacetamido)-Thienamycin Methyl and Benzyl Esters Hydrobromide Salts A solution of 36 mg. of N-bromoacetyl-Thienamycin methyl ester and 150 mg. of thiourea in 4 ml. of dioxane is kept at 23° C. for 18 hours. The addition of 50 ml of ether gives a precipitate of N-(guanylthioacetamido)-thienamycin methyl ester as the hydrobromide which is recovered by filtration. The corresponding hydrobromide of N-(guanylthioacetamido)-thienamycin benzyl ester is prepared by following the same procedure except that the benzyl ester is prepared by following the same procedure except that the benzyl ester is substituted for the methyl ester.

EXAMPLE 19

Preparation of N-(Bromo-t-Butoxycarbonyl)thienamycin p-Bromophenacyl Ester

Step A: Preparation of N-Bromo-t-Butoxycarbonyl-O-TMS-Thienamycin-TMS Ester

Th(TMS)3 (16 mg.) is dissolved in 0.4 ml. of dry tetrahydrofuran to which is added 20 $\mu$l (28 mg., 0.13 mmole) of bromo-t-butylchloroformate (b.p. 35°/0.9 mm) and 8 $\mu$l (5.67 mg., 0.057 mmole) of triethylamine (redistilled from BaO). The mixture is shaken at 25° C. for 20 min. Evaporation of solvent and excess reagents gives crude desired product. UV$\lambda_{max}$$^{CH3CO2CH2CH3}$ 320 nm (E9,000).

Step B: Preparation of N-(Bromo-t-Butoxycarbonyl)-thienamycin

The product of Step A (3 mg.) is dissolved in 0.5 ml. of ph 7 phosphate buffer and 0.1 ml. of tetrahydrofuran and the solution left at 25° C., for 20 minutes. The solution is then passed down a column (5 ml.) of Dowex 50×8 (Na+ form) and the eluate fractions monitored by U.V. The correct fractions are combined and freeze dried to yield the desired product. UV$\lambda_{max}$$^{buffer}$ 304 nm (e=9,300); electrophoresis at 50 V/Cm. 20 min in pH 7.0 buffer shows a single bioactive zone which moves 31.5 mm towards the anode.

Step C: Preparation of N-(Bromo-t-Butoxycarbonyl)-thienamycin p-Bromophenacyl Ester The product of Step B (13 mg. 0.022 mmole) is dissolved in 0.4 ml. of tetrahydrofuran. To this solution is added p-bromophenacyl bromide (9.6 mg., 0.035 mmol) and 20 μl (14.4 mg., 0.14 mmole) of triethylamine. The mixture is shaken at 25° C. for 30 min. and then evaporated to dryness. Ten ml. of ether is added to the residue and the mixture treated with 0.2 ml. of 0.1 M pH 7.0 phosphate buffer.

The organic layer is separated, dried over sodium sulfate, concentrated to 0.5 ml. and applied to two 20×20 cm., 250μ silica gel GF tlc plates which are developed with 20% ethyl acetate in chloroform. ($R_f$=0.65) the desired product (6.7 mg.) is isolated in 42% yield.

EXAMPLE 20

Preparation of N-Glycyl thienamycin 3-Methyl-2-butene 1-yl Ester

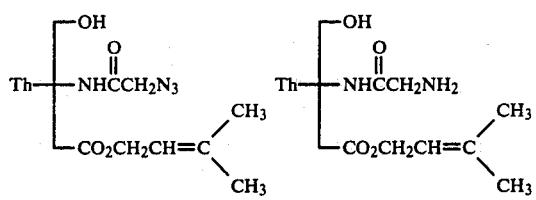

N-Azidoacetyl thienamycin 3-methyl-2-butene-1-yl ester (10 mg.) is dissolved in ethyl acetate (1 ml.). This solution is added to the hydrogenation flask containing 10 mg. of palladium (from palladium oxide) and 0.5 ml. 50% methanol in ethyl acetate. The mixture is stirred under 1 atm hydrogen at 25° C. for 1 hour, then the mixture is filtered from the catalyst. The desired product is isolated by TLC ($R_f$=0.16, in 20% methanol/chloroform). Electrophoresis of the product at pH 7.0 buffer (50 V/cm, 20 min.) shows one bio-active band which moves 34 mm towards the cathode Uv $\lambda_{max}^{ethanol}$ 315 nm, IR (CHCl$_3$): 3300 (NH$_2$), 1777 (β-lactam), and 1672 cm$^{-1}$ (ester and amide).

EXAMPLE 21

Preparation of N-Azidoacetyl thienamycin p-t-Butylbenzyl Ester

N-Azidoacetyl thienamycin sodium salt (136 mg., 0.36 mmole) stirred with HMPA (5 ml.) and p-t-butylbenzyl bromide (180 mg., 0.79 mmole) at 25° C. for 30 min. The solution is diluted with 10 ml. ethyl acetate and washed thoroughly with water. The organic layer is separated and dried over sodium sulfate. The desired product (80 mg.) is isolated by silica gel TLC ($R_f$=0.18 in ethyl acetate). IR (CHCl$_3$): 2121 (N$_3$) 1777 (β-lactam) and 1684 cm$^{-1}$ (ester and amide); Pmr (CDCl$_3$, 60 MHz): 1.32 (s, t-Bu), 1.34 (d, C$\underline{H}_3$CH), 2.60-3.75 (m, 3C$\underline{H}_2$ and C$_6$-$\underline{H}$), 3.90 (s, C$\underline{H}_2$N$_3$), 4.30 (m, C$_5$-H and C$_7$-$\underline{H}$),

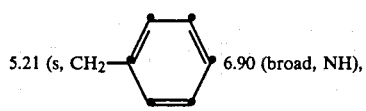

5.21 (s, CH$_2$—), 6.90 (broad, NH), and 7.33 ppm (s, aromatic protons).

EXAMPLE 22

Preparation of N-Glycyl thienamycin p-t-Butylbenzyl Ester

N-Azidoacetyl thienamycin p-t-butylbenzyl ester (10 mg.) is dissolved in 0.5 ml. ethyl acetate. The solution is added to the hydrogenation flask containing 50 mg. of palladium (from palladium oxide) and 0.5 ml. ethyl acetate. The mixture is stirred under 1 atm hydrogen at 25° C. for 10 minutes. TLC indicates (as in Example 24) that all the starting material is consumed. The reaction mixture is filtered from the catalyst and evaporated to dryness to give the crude product. IR (CHCl$_3$): 1776 (β-lactam) and 1675 (ester and amide); Uv $\lambda_{max}^{ethanol}$ 320 nm and 275 nm; Pmr (CHCl$_3$ 60 MHz): 1.32 (s, t-Bu), 1.34 (d, C$\underline{H}_3$CH), 5.23

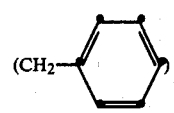

and 7.33 ppm (s, aromatic protons).

EXAMPLE 23

Preparation of N-Azidoacetyl thienamycin Pivaloxymethyl Ester

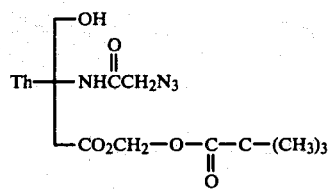

N-Azidoacetyl thienamycin sodium salt (11.0 mg., 0.04 mmole) is stirred with HMPA (1 ml.) and chloromethyl pivalate (36 mg., 0.24 mmole) at 25° C. for 30 min. The mixture is diluted with ethyl acetate and washed with water. The desired product is isolated by silica gel TLC ($R_f$=0.18 in ethyl acetate)IR (CHCl$_3$): 2121 (N$_3$), 1777 $c^{m-1}$ (β-lactam); Pmr (CDCl$_3$, 60 MHz); 1.22 (s, t-Bu), 1.32 (d, C$\underline{H}_3$CH), 3.98 (S, C$\underline{H}_2$N$_3$), and 5.83 ppm (dd, CO$_2$C$\underline{H}_2$O-).

EXAMPLE 24

Preparation of N-Azidoacetyl thienamycin 2-Methyl-2-Propene-1-yl Ester

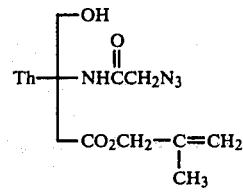

N-Azidoacetyl thienamycin lithium salt (20 mg., 0.055 mmole) is stirred with HMPA (1 ml.) and 3-chloro-2-methylpropene 27 mg., 0.30 mmole) for 30 min. at 25°. The mixture is diluted with ethyl acetate and washed wtih water. The desired product is isolated by silica gel TLC $R_f$=0.18 in ethyl acetate) IR (CHCl$_3$): 2121 (N$_3$), 1777 (β-lactam), and 1684 cm$^{-1}$ (ester and amide).

EXAMPLE 25

Preparation of N-Glycyl thienamycin Esters

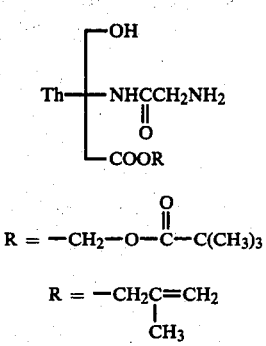

$R = -CH_2-O-\overset{O}{\underset{\|}{C}}-C(CH_3)_3$   I.

$R = -CH_2C=CH_2$   II.
      $\phantom{R = -CH_2}|$
      $\phantom{R = -CH_2}CH_3$ Compounds I-II are prepared respectively, when the corresponding starting material is substituted in equivalent amount in the reduction process of Example 20, for the preparation of N-azidoacetyl thienamycin 3-methyl-2-butene-1-yl ester.

EXAMPLE 26

Preparation of N-Benzyloxycarbonyl thienamycin and N-Benzyloxycarbonyl Benzylcarbonic Acid Anhydride

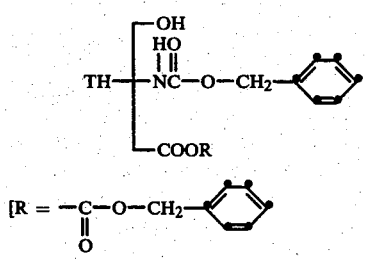

A solution of 16.6 mg. of Thienamycin in 4 ml. of 0.05 M pH 7 phosphate buffer and 2 ml. of dioxane in a 3-necked flask fitted with a stirrer, thermometer, pH electrode and the delivery tip of an automatic titrator is cooled to $-8°$ C. in a methanol-ice bath. The pH is brought to 8.2 by the addition of 0.2 N sodium hydroxide in 50% aqueous dioxane and a solution of 0.015 ml of carbobenzyloxy chloride in 2 ml. of chloroform is added. The mixture is stirred at $-6°$ C., pH 8.2, for ten minutes, then layered with ether and the pH adjusted to 7 by the addition of N hydrochloric acid. The layers are separated by centrifugation and the aqueous phase is extracted twice again with ether. The aqueous phase is layered with ethyl acetate and acidified to pH 2. The ethyl acetate is separated and the aqueous layer is extracted again with ethyl acetate. The combined ethyl acetate layer is washed with saturated sodium chloride solution, dried over magnesium sulfate and filtered. The filtrate is stirred with water and the pH brought to 7 by the addition of dilute sodium bicarbonate solution. The aqueous phase is separated and freeze dried giving the sodium salt of N-benzyloxycarbonyl Thienamycin Weight 10 mg. (b 46%). The UV spectrum, $\lambda_{max}$ 303 mμ, E% 174 (E 6,290) indicates about 80% purity. Electrophoresis at 50 V/cm. for 20 minutes at pH 7 followed by bioautograph on S. aureus gives a zone of inhibition at +2.5 cm.

The ethereal extracts of the reaction mixture contain the desired product N-benzyloxycarbonyl thienamycin benzyl carbonic acid anhydride. UV $\lambda_{max}$ 335 mμ.

EXAMPLE 27

Preparation of N-Benzyloxycarbonyl thienamycin Benzyl Ester

The N-Benzyloxycarbonyl thienamycin [Example 26], in EtOAc is carried through the procedure of Example 26, except that an equivalent amount of phenyldiazomethane is added to the dried EtOAc solution from the pH 2 extraction and the solution left at 4° for 2 hours. Evaporation to dryness yields crude N-benzyloxycarbonylthienamycin benzyl ester which is isolated by thin layer chromatography $R_f$ 0.24 3:1 ethyl acetate chloroform. It crystallizes from ether. IR 5.63μ (lactam carbonyl); shoulder 5.8μ (ester); 5.88μ (urethane carbonyl). UV, dioxane, $\lambda_{max}$ 318 mμ, E% (E=10,900). m/e M+ 496.

EXAMPLE 28

Preparation of N-Carbomethoxy thienamycin p-pivaloyloxybenzyl Ester

Step A: N-Carbomethyl thienamycin

Thienamycin (49 mg., 148μ mol) is dissolved in 0.05 M pH 7 phosphate buffer (14 m.) and cooled in an ice bath. With stirring the pH is adjusted to 8.2 using an automatic burette. A solution of methyl chloroformate (46 μl, 600 μmol) in p-dioxane (580 μl) is added at once to give a homgeneous solution. Subsequently, the pH is maintained at 8.2 using the automatic burette. After 10 min., the solution is adjusted to pH 7 using dilute phosphoric acid solution and washed three times with an equal volume of diethyl ether. The aqueous solution is then concentrated to 4.5 ml. and chromatographed on an XAD-2 resin column. The product is eluted (after water elution) with an aqueous 5% tetrahydrofuran solution and is freeze-dried to give 28.9 mg. of product. UV (pH 7 phosphate buffer 0.1 N). $\lambda_{max}$ 303 nm (e 6,450) Electrophoresis (20 min., 0.1 N pH 7 phosphate buffer, 50 v/cm) mobility 3.5 cm to cathode.

Step B: N-Carbomethoxy thienamycin p-pivaloyloxybenzyl Ester

Following the procedure of Example 21 and substituting in equivalent amounts: N-carbomethoxy thienamycin (as its sodium salt) and p-pivaloyloxybenzyl bromide for the N-aziodoacetyl thienamycin sodium salt and p-t-butylbenzyl bromide, respectively, the title is obtained.

EXAMPLE 29

Preparation of N-Benzenesulfonyl thienamycin 2-Methyl-2-propen-1-yl Ester

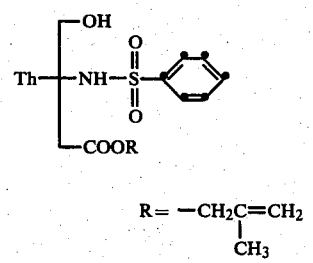

$R= -CH_2C=CH_2$
  $\phantom{R= -CH_2}|$
  $\phantom{R= -CH_2}CH_3$

Step A: N-Benzenesulfonyl thienamycin

Thienamycin (52 mg. 148 μmol) is dissolved in pH 7 0.1 N phosphate buffer (25 ml.) and magnetically stirred in an ice bath. The pH is adjusted to 8.2 with 2.5 N NaOH using an automatic dispensing burette and benzenesulfonyl chloride (227 μl, 226 μmol) in 500 ml. p-dioxane added at once. The pH is maintained at 8.2 (using the automatic burette) for 30 min. and then adjusted to pH 7.0 with dilute aqueous phosphoric acid. The reaction solution is concentrated to 15 ml. and chromatographed on XAD-2 resin (50 cc). The column is eluted with water, then with 10% aqueous tetrahydrofuran which elutes the product. The 10% aqueous tetrahydrofuran eluate is concentrated to ⅓ volume and freeze-dried to give 28 mg. Electrophoretic mobility of the product (50 v/cm, 20 min., pH 7 0.05 N phosphate buffer) is 3.5 cm towards the cathode. $\lambda_{max}$ 303 ($\epsilon$3, 650), in pH 7 0.1 N phosphate buffer).

Step B: N-Benzensulfonyl thienamycin 2-Methyl-2-propen-1-yl Ester

Following the procedure of Example 21 and substituting in equivalent amounts N-Benzensulfonyl thienamycin (as its sodium salt) and 2-methyl-2-propen-1-yl chloride for the N-azidoacetyl thienamycin sodium salt and p-t-butylbenzyl bromide respectively, the title compound is obtained.

EXAMPLE 29a

Preparation of N-[N'-Acetimidoyl-β-alanyl]Thienamycin p-t-Butylbenzyl Ester

Step A: N-[β-Azidopropionyl]Thienamycin

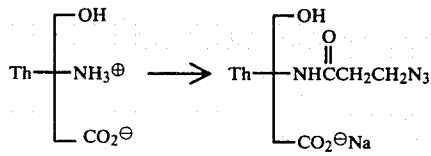

Thienamycin (184 mg) is dissolved in 30 ml. of water and is kept at 0° C. To the solution is added 0.52 g of NaHCO₃, 30 ml of dioxane and 163 mg of β-azidopropionyl chloride. The mixture is stirred for 15 minutes then is neutralized with 30% H₃PO₄, extracted with ether. The aqueous layer is separated and concentrated to 5 ml. The crude product is chromatographed on a Dowex 50W×8 (Na form) ion-exchange column (1"×10"). The column is eluted with H₂O to give 81 mg of the desired product which shows uv absorption at $\lambda_{max}^{H2O}$ 306 nm. Electrophoresis of the product at 2 KV in 0.1 M pH 7.0 phosphate buffer for 2 hours shows a single bioactive zone which moves 30 mm toward anode.

Step B: N-(β-Alanyl)Thienamycin

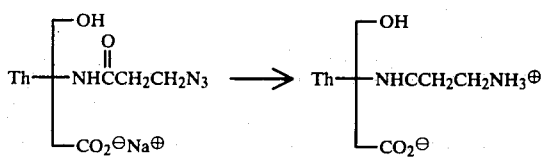

The aqueous solution of N-(β-azidopropionyl)-Thienamycin (40 mg in 20 ml water) is hydrogenated under 1 atm of hydrogen in the presence of 200 mg of palladium at 25° C., for 40 minutes. The resultant solution of (pH 9.0) is neutralized with 30% H₃PO₄ and filtered from the catalyst. The mixture is chromatographed on a Dowex 50W×8 (Na form) ion-exchange column (1"×10") and the column is eluted with water to give 20 mg of the desired product which shows uv $\lambda_{max}^{H2O}$ 302 nm. Electrophoresis of the product at 2 KV in 0.1 M pH 7.0 phosphate buffer for 20 min. shows single bioactive zone which moves 10 mm toward cathode.

Step C: N-[N'-Acetimidoyl-β-alanyl]Thienamycin

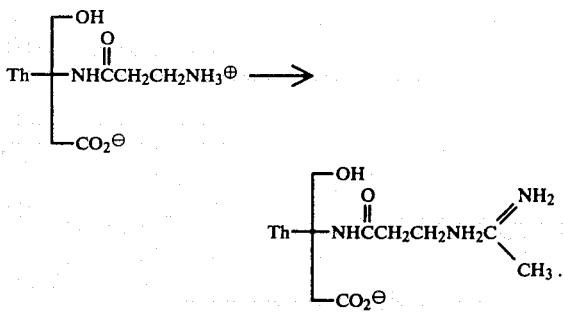

The aqueous solution of N-(β-alanyl)thienamycin (125 mg in 15 ml water) is kept at 0° C. and maintained at pH 8.5 by adding 2.5 N NaOH while O-ethylacetimidate hydrochloride (350 mg) is added portionwise to the solution during a period of 10 min. The mixture is stirred for 1 hour then is neutralized with 2.5 N HCl and concentrated to 15 ml. The crude product so obtained is chromatographed twice on Dowex 50W×8 (Na form) column (1"×10") to yield 25 mg. The product is eluted with water and the solution lyophylized. Recrystallization of the product from water gives a crystalline solid which shows ir (Nujol mull): 1769 cm⁻¹ (β-lactam); nmr (D₂O, 100 MHz): 2.20 ppm (s, acetimidoyl C$\underline{H}_3$); uv $\lambda_{max}^{H2O}$ 302 nm. Electrophoresis of the product at 2 KV in 0.1 M pH 7.0 phosphate buffer for 20 min shows single bio-active zone which moves 10 mm toward cathode.

Step D: N-[N'-Acetimidoyl-β-alanyl]Thienamycin-p-t-Butylbenzyl Ester

Following the procedure of Example 21, the title compound is obtained when the indicated substitutions are made.

EXAMPLE 29b

Preparation of N-Bromo-t-butyloxycarbonyl Thienamycin Sodium Salt

Method A: Thienamcyin (190 mg) dissolved in 15 ml 0.1 M pH 7.0 phosphate buffer and 15 ml dioxane is kept at 0° C. The solution is adjusted and maintained between pH 8.5-9.0 with 1 N NaOH while 480 mg of bromo-t-butyl chloroformate is added to the solution during a period of 5 minutes. The mixture is stirred for 30 min., then is neutralized to pH 7.0 with 1 N HCl and extracted with ether. The aqueous layer is separated, concentrated to 10 ml and chromatographed on a Dowex-50×8 (Na form) column (1.5Δ×10") which is eluted with H₂O to give 113 mg of the desired product. Lyophilization of the solution gives solid product.

Method B: Thienamycin (95 mg) in 10 ml 0.1 M phosphate buffer and 10 ml dioxane is kept at 0° C. The solution is adjusted and maintained between pH 8.5-9.0 while 240 mg of bromo-t-butyl chloroformate is added. The mixture is stirred for 30 minutes, then is acidified to pH 2.0 with H₃PO₄. The acidified solution is extracted with 2×25 ml ethylacetate. The organic layer is separated and back extracted with 10 ml NaHCO₃ solution which contains 30 mg of NaHCO₃. The aqueous layer containing 30 mg of the desired product is lyophilized to give solid product. Nmr (60 MHz, D₂O): ϵ1.26(d), 1.60(s), 2.65–3.50(m), 3.70(s), and 3.90–4.20(m). UV $\lambda_{max}^{D_2O}$ 303 nm.

EXAMPLE 29c

Preparation of N-Bromo-t-butyloxycarbonyl Thienamycin p-Nitrobenzyl Ester

The lyophilized N-bromo-t-butyloxycarbonyl-thienamycin sodium salt (100 mg) is stirred at 25° C., with p-nitrobenzyl bromide (300 mg) in 2 ml hexmethylphosphoramide for 1 hour. The mixture is diluted with 10 ml ethylacetate then is washed thoroughly with water. The organic layer is separated, dried over Na₂SO₄ and chromatographed on two 250μ silica gel GF TLC plates using ethylacetate is solvent (R_f 0.45) to give 50 mg of the desired product. IR (CDCl₃): 1777 (β-lactam) and 1711 cm⁻¹ (ester); UV $\lambda_{max}^{EtOH}$ 270 nm and 322 nm; NMR (CDCl₃60 MHz): δ1.38(d), 1.58(s), 2.60–3.80(m), 3.78(s), 3.90–4.20(m), 5.30(s), 7.55(d) and 8.30 ppm (d).

EXAMPLE 30

Preparation of O-Dibenzylphosphoryl-N-(p-nitrobenzyloxycarbonyl) Thienamycin-p-nitrobenzyl Ester

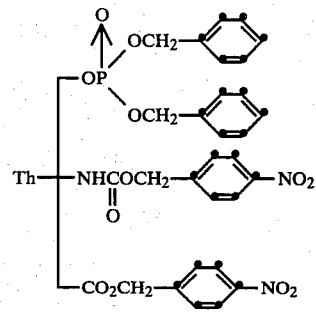

Step A:

To a solution of N-(p-nitrocarbobenzyloxy)-Thienamycin-(p-nitrobenzyl)-Ester (50 mg) in 5 ml THF at 3° C. is added 30 mg. of dibenzyl phosphorochloridate followed by 14 μl of triethylamine. The mixture is stirred at 25° C. for 22 hours. whereupon the THF is removed in vacuo. The residue is taken up in methylene chloride and washed with water. The methylene chloride solution is dried over magnesium sulfate and evaporated. The residue is chromatographed on silica gel yielding O-dibenzylphophoryl-N-(p-nitrobenzyloxycarbonyl Thienamycin p-nitrobenzyl ester.

EXAMPLE 31

Preparation of O-(Methylcarbamoyl)-N-p-nitrobenzyloxycarbonyl-Thienamycin-p-nitrobenzyl Ester

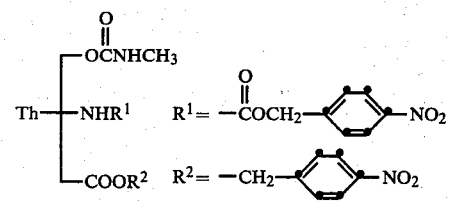

A solution of N-(p-nitrobenzyloxycarbonyl)-Thienamycin-(p-nitrobenzyl)ester (20 mg) and methylisocyanate (20 mg) in methylene chloride (5 ml) is stirred at 23° C. for 18 hours. The solvent is evaporated and the residue is extracted with hexane. The hexane insoluble residue is chromatograaphed on silica gel giving substantially pure O-(Methylcarbamoyl)-N-p-nitrobenzyloxycarbonyl-Thienamycin-p-nitrobenzyl ester.

EXAMPLE 32

Preparation of O-(Methoxymethyl)-N-(p-nitrobenzyloxycarbonyl-Thienamycin-p-nitrobenzyl Ester

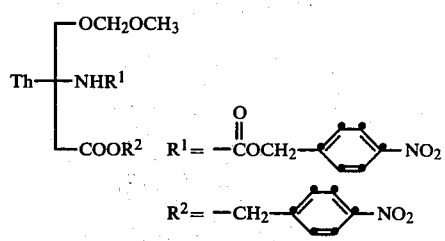

Step A:

A solution of 58 mg. of p-nitrobenzyloxycarbonyl-Thienamycin-p-nitrobenzyl ester in 5 ml. of 1.0 ml. of THF and HMPA is cooled to −78° C. To this solution is added with stirring a 2 N solution of phenyllithium (0.1 ml) immediately sollowed by the addition of 0.2 ml of methylchloromethyl ether. The mixture is allowed to warm to 25° C. during a period of one hour. Methylene chloride (25 ml) is added and the solution is extracted wtih 0.1 N, pH7, phosphate buffer (25 ml) and water 4×25 ml. The methylenechloride solution is evaporated and the residue is triturated with hexane. The hexane insoluble residue is chromatographed on silica gel yielding O-methoxymethyl-N-(p-nitrobenzyloxycarbonyl-Thienamycin-(p-nitrobenyl)ester.

EXAMPLE 33

Preparation of O-Methyl-N-Benzyloxycarbonyl-Thienamycin-Benzyl Ester

A solution of 5 mg. of N-carbobenzyloxy thienamycin benzyl ester in 0.3 ml of methylene chloride is cooled to 0° C. and 0.1 ml. of a 0.006 M solution of fluoboric acid in 5:1 ether-methylene chloride is added, followed immediately by 0.5 ml. of 0.1 M diazomethane in methylene chloride. The solution is decolorized in 1 minute. The mixture is stirred with ether and pH 7 phosphate buffer and the ethereal phase is evaporated. The residue is chromatographed on 2×8″ 250μ silica plates in 35% ethyl acetate-chloroform. The band at R_f 0.5 is eluted with ethyl acetate. Measurement of the U.V. absorbance at 318 mμ shows a 13% recovery of the initial optical density. Mass spectrum analysis shows m/e M+ 510 and fragments at m/e 410, 59, 333 and 478 characteristic of O-methyl-N-benzyloxycarbonyl-Thienamycin benzyl ester.

Alternate Preparation
O-Methyl-N-Benzyloxycarbonyl-Thienamycin-Benzyl Ester

A solution N-benzyloxycarbonyl-Thienamycinbenzyl ester (5 mg.) in 0.2 ml. dry THF is cooled to −78° C. To this solution is added 5 μl of phenyllithium solution (2 N) followed immediately by 1 μl of methylfluorosulfonate. The mixture is stirred at −78° C. for 20 minutes and is then diluted with 2 ml. of ether and extracted with 2 ml. of 0.01 N pH 7 phosphate buffer. The ethereal layer is evaporated nd the residue is chromatographed on a 2"×8" thin layer silica gel plate in 1:1 ethylacetate-chloroform. The band at $R_f=0.63$ is isolated giving the desired product, O-Methyl-N-benzyloxycarbonyl-Thienamycin-benzyl ester.

EXAMPLE 34

Preparation of O-Acetyl-N-(p-Nitrobenzyloxycarbonyl)-Thienamycin-(p-Nitrobenzyl)-Ester

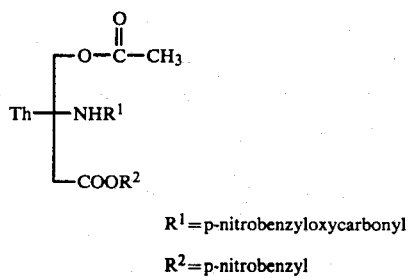

$R^1$ = p-nitrobenzyloxycarbonyl $R^2$ = p-nitrobenzyl

To a solution of 50 mg. of N-(p-nitrobenzyloxycarbonyl)-Thienamycin-(p-nitrobenzyl)ester in 0.5 ml. pyridine is added 0.16 ml. of acetic anhydride. The mixture is allowed to react at 250° C., for 3 hours, then pumped to drynesss under vacuum. The solid residue is dissolved in chloroform and chromatographed on an 8"×8" silica gel plate in 3:1 ethylacetate-chloroform. The band at $R_f$ 0.55 is isolated yielding 36 mg. of O-acetyl-N-(p-nitrobenzyloxycarbonyl)-thienamycin-(p-nitrobenzyl)ester; m.p. 172°-175° C. NMR (CDCl₃) δ, 1.41, (d J=6 HZ C$\underline{H}_3$); 2.04 (s COCH₃), 2.7-3.6 (m); 4.14 (t of d) (J=3 and 9 Hz); 5.17 (s, carbamyl C$\underline{H}_2$); 5.35 (AB quartet, J=14 Hz), 7.45 (d), 7.60 (d), 8.18 (d) (J=9 Hz, aromatic H) Ms. M+ m/e 628.

EXAMPLE 35

Preparation of N-(p-Nitrobenzyloxycarbonyl)Thienamycin O-methanesulfonyl p-nitrobenzyl ester

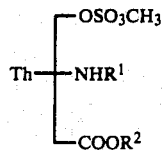

$R^1$ = p-nitrobenzyloxycarbonyl $R^2$ = p-nitrobenzyl

Methanesulfonyl chloride (34 mg.) in CH₂Cl₂ (0.8 ml.) is added dropwise over 5 minutes to an ice-cold, stirred solution of N-(p-nitrobenzyloxycarbonyl)-Thienamycin-p-nitrobenzyl ester (117 mg.) and triethylamine (40 mg.) in anhydrous CH₂Cl₂ (6 ml.). After stirring for 1.5 hours more, the reaction mixture is diluted with cold CH₂Cl₂ (20 ml.), washed with water (3" C., 10 ml.), 0.1 M pH 3 phosphate buffer (3° C., 5 ml.), and 2% aqueous NaHCO₃ (3° C.), dried with MgSO₄ and filtered. Evaporation of the solvent in vacuo leaves p-nitrobenzyl-6-(1-methanesulfonyloxyethyl)-3-[2-(p-nitrobenzyloxycarbonylamino)ethylthio]-7-oxo-1-azabicyclo[3.2.0]-hept-2-ene-2-carboxylate (otherwise referred to as N-(p-nitrobenzyloxycarbonyl)Thienamycin O-methanesulonyl p-nitrobenzyl ester, for convenience) as an oil.

EXAMPLE 36

When the N-acyl thienamycin carboxylic esters of Examples 8-29b are substituted, in equivalent amounts for the N-acyl thienamycin carboxylic ester starting materials of Examples 2-7 and 30-35, the corresponding O-, N- and carboxyl thienamycin derivatives of the present invention are obtained.

EXAMPLE 37

Following the procedures set out in the foregoing Examples and text the following compounds of the present invention are obtained:

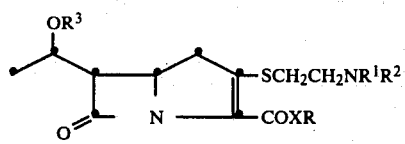

| Compound | $R^3$ | R | $R^2$ | X | $R^1$ |
|---|---|---|---|---|---|
| (1.) | —C(=O)—H | —CH₂—(phenyl) | H | O | H |
| (2.) | —C(=O)—NH₂ | —CH₂—O—C(=O)—C(CH₃)₃ | H | O | H |
| (3.) | —C(=O)—S—CH₃ | —CH₂CH₂—S—CH₃ | —C(=O)—H | O | H |
| (4.) | —C(=O)—O—CH₃ | —CH₂—CH₂—N(CH₃)₂ | —C(=O)—O—CH₃ | O | H |
| (5.) | —C(=O)—CH₂Br | —CH₂CH₂=CH₂ | —C(=O)—CH₂Br | O | H |
| (6.) | —C(=O)—CH₂NH₂ | H | —C(=O)—CH₂NH₂ | O | H |

-continued

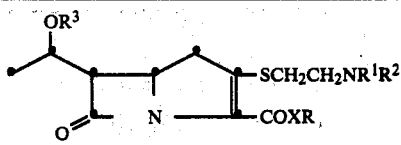

| Compound | R³ | R | R² | X | R¹ |
|---|---|---|---|---|---|
| (7.) | -C(=O)-CH₂-N(CH₃)₂ | H | -C(=O)-CH₂-N=C(NH₂)(CH₃) · HCl | O | H |
| (8.) | -C(=O)-CH₂OH | -CH₂-C(=CH₂)-CH₃ | -C(=O)-N(H)-CH₃ | O | H |
| (9.) | -C(=S)-S-CH₃ | -CH₂-S-C(=O)-CH₃ | -C(=O)-CH₂Cl | O | H |
| (10.) | -C(=O)-CH₂-O-CH₃ | -CH₂-C(=O)-φ | -C(=O)-CH₂CH₂NH₂ | O | H |
| (11.) | -C(=NH)(NH₂) · HCl | -CH₂-CH₂-C(CH₃)=CH₃ | -C(=O)-CH₂C≡CH | O | H |
| (12.) | -C(=O)-CH₂-N(H)-C(=NH)-NH₂ | H | -C(=O)-CH₂-N=C(H)-NH · H₂SO₄ | O | H |
| (13.) | -C(=O)-(CH₂)₂-N(H)-C(=NH)-NH₂ · H₃PO₄ | -CH₂-CH₂-CH=CH₂ | H | O | H |
| (14.) | -C(=O)-CH₂-COOH | -CH₂-O-C(=O)-O-CH₃ | -C(=O)-CH₂-S-C(=NH)(NH) | O | H |
| (15.) | -SO₃H | -CH₂-φ-O-C(=O)-CH₃ | H | O | H |
| (16.) | -P(=O)(N(CH₃)₂)₂ | -CH₂-O-C(=O)-C₂H₅ | -C(=O)-CH₂N⁺(CH₃)₃Cl⁻ | O | H |
| (17.) | -SO₂NH₂ | (methyl-dihydrofuranone) | -C(=O)-O-CH₂φ | O | H |
| (18.) | -SO₂N(CH₃)₂ | -CH₂-φ-O-CH(CH₃)₂ | -C(=O)-O-CH₂φ-NH₂ | O | H |
| (19.) | -CH₂-N(CH₃)₂ | -CH₂-S-C(=O)-CH(CH₃)₂ | -C(=O)-O-C(CH₂Br)(CH₃)₂ | O | H |
| (20.) | -CH₂CH₂-OH | -CH₂-O-CH₃ | -C(=O)-CF₃ | O | H |
| (21.) | -CH₂CH₂-N(C₂H₅)₂ | -C₂H₅ | -C(=O)-O-CH₂CF₃ | S | H |
| (22.) | -CH₂-C(=O)-CH₃ | Na | -C(=O)-CH₂-O-φ | S | H |
| (23.) | -CH₂-C(=O)-φ | K | -S-φ(NO₂) | O | H |
| (24.) | -CH₂-S-CH₃ | -CH₂-S-CH₃ | -C(=O)-CH₂CH₂-N(H)-C(CH₃)=NH · HCl | O | H |

-continued

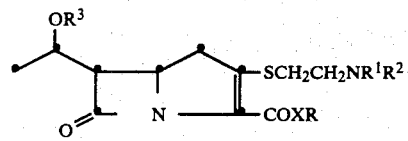

| Compound | R³ | R | R² | X | R¹ |
|---|---|---|---|---|---|
| (25.) | —Si(CH₃)₃ | —CH₃—⌬—OCH₃ | —C(=O)—N(H)—CH₃ | O | H |
| (26.) | O=C(OCH₂)—⌬—O—CH₃ | —CH₂—OCH₂—⌬—OCH₃ | —P(=S)(ONa)(OCH₃) | O | H |
| (27.) | —C(=O)—CH₂CCl₃ | —CH₂—⌬—NO₂ | —C(=O)—C≡CH | O | H |
| (28.) | O=C—C(CH₂Br)(CH₃)₂ | O—CH₂—O—C(=O)—N—(CH₃)₂ | —S—CF₃ | O | H |
| (29.) | —C—O—CH₂—(fluorenyl) | O—CH₂—N(H)—C(=O)—CH₃ | —C(=O)—S—CH₃ | O | H |
| (30.) | —CH₂—O—C(=O)—CH₃ | —CH₂—O—C(=O)—CH₃ | —P(=O)(O—CH₃)(OCH₃) | O | H |

EXAMPLE 38

Preparation of Pharmaceutical Compositions

One such unit dosage form consists in mixing 120 mg. O-methanesulfonyl-N-glycyl-thienamycin-(3-methyl-2-butene-1-yl) ester with 20 mg. of lactose and 5 mg. of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
|---|---|
| O-methanesulfonyl-N-glycyl thienamycin -(3-methyl-2-butene-1-yl) | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with 15% cornstarch paste (6 mg.) and rough-screened. It is dried at 45° C. and screened gain through No. b 16 screens. The balance of the cornstarch and the magnesium stearate is added and the mixture is compressed into tablets, approximately 0.5 inch in diameter each weighing 800 mg.

| PARENTERAL SOLUTION | | |
|---|---|---|
| Ampoule: | | PER TABLET |
| O-methanesulfonyl-N-glycyl-thienamycin (3-methyl-2-butene-1-yl) | | 500 mg. |
| Diluent: Sterile Water for Injection | | 2 cc. |
| OPTHALMIC SOLUTION | | |
| O-methanesulfonyl-N-glycyl-thienamycin (3-methyl-2-butene-1-yl) | | 100 mg. |
| Hydroxypropylmethyl Cellulose | | 5 mg. |
| Sterile Water | to | 1 ml. |
| OTIC SOLUTION | | |
| O-methanesulfonyl-N-glycyl-thienamycin (3-methyl-2-butene-1-yl) | | 100 mg. |
| Benzalkonium Chloride | | 0.1 mg. |
| Sterile Water | to | 1 ml. |
| TOPICAL OINTMENT | | |
| O-methanesulfonyl-N-glycyl-thienamycin (3-methyl-2-butene-1-yl) | | 100 mg. |
| Polyethylene Glycol 4000 U.S.P. | | 400 mg. |
| Polyethylene Glycol 400 U.S.P. | | 1.0 gram |

The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. The compound having the trans- form of the structure of the following formula:

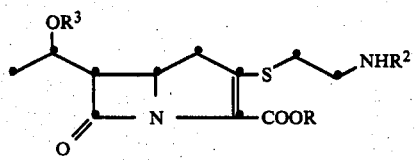

wherein r is hydrogen, a pharmaceutically acceptable salt cation, or an easily removable blocking group; $R^3$ is $SO_3H$ or $SO_3CH_3$; and $R^2$ is formyl, acetyl, propionyl, butyryl, chloroacetyl, methoxyacetyl, aminoacetyl, methoxycarbonyl, ethoxycarbonyl, methylcarbamoyl, ethylcarbamoyl, phenylthiocarbonyl, 3-aminopropionyl, 4-aminobutyryl, N-methylaminoacetyl, N,N-dimethylaminoacetyl, N,N,N-trimethylaminoacetyl, 3-(N,N-dimethyl)aminopropionyl, 3-(N,N,N-trimethyl)amino propionyl, N,N,N-triethylaminoacetyl, pyridiniumacetyl, guanylthioacetyl, guanidinoacetyl, 3-guanidinopropyl, $N^3$-methylguandinopropionyl, hydroxyacetyl, 3-hydroxypropionyl, acryloyl, propynoyl, malonyl, phenoxycarbonyl, amidinoacetyl, acetamidinoacetyl, amidinopropionyl, acetamidopropionyl, guanylureidoacetyl, guanylcarbamoyl, carboxymethylamino-acetyl, sulfoacetylaminoacetyl, phosphonoacetylaminoacetyl, $N^3$-dimethylaminoacetamidinopropionyl, ureidocarbonyl, dimethylguanylthioacetyl, 3-(1-methyl-4-pyridinium)propionyl, 3-(5-aminoimidazol-1-yl)propionyl, 3-methyl-1-imidazoliumacetyl, 3-sydnonylacetyl, o-aminomethylbenzoyl, or o-aminobenzoyl.

2. An antibiotic pharmaceutical composition comprising a therapeutically effective amount of a compound according to claim 1 and a pharmaceutical carrier therefor.

* * * * *